US012319901B2

(12) United States Patent
Luro et al.

(10) Patent No.: US 12,319,901 B2
(45) Date of Patent: Jun. 3, 2025

(54) ISOLATING LIVE CELLS AFTER HIGH-THROUGHPUT, LONG-TERM, TIME-LAPSE MICROSCOPY

(71) Applicant: President and Fellows of Harvard College, Cambridge, MA (US)

(72) Inventors: Scott Luro, Cambridge, MA (US); Burak Okumus, Cambridge, MA (US); Johan Paulsson, Cambridge, MA (US)

(73) Assignee: PRESIDENT AND FELLOWS OF HARVARD COLLEGE, Cambridge, MA (US)

(*) Notice: Subject to any disclaimer, the term of this patent is extended or adjusted under 35 U.S.C. 154(b) by 656 days.

(21) Appl. No.: 17/620,636

(22) PCT Filed: Jun. 22, 2020

(86) PCT No.: PCT/US2020/038867
§ 371 (c)(1),
(2) Date: Dec. 17, 2021

(87) PCT Pub. No.: WO2020/257746
PCT Pub. Date: Dec. 24, 2020

(65) Prior Publication Data
US 2022/0348854 A1 Nov. 3, 2022

Related U.S. Application Data

(60) Provisional application No. 62/864,091, filed on Jun. 20, 2019.

(51) Int. Cl.
*C12M 3/06* (2006.01)
*C12M 1/00* (2006.01)
(52) U.S. Cl.
CPC ............ *C12M 23/16* (2013.01); *C12M 47/04* (2013.01)

(58) Field of Classification Search
CPC ................... C12M 23/16; C12M 47/04; B01L 2400/0487; B01L 3/502746; B01L 3/502761
See application file for complete search history.

(56) References Cited

U.S. PATENT DOCUMENTS

| 6,767,706 B2 | 7/2004 | Quake |
| 8,075,748 B2 | 12/2011 | McAllister |
| (Continued) | | |

FOREIGN PATENT DOCUMENTS

| JP | 2016521350 A | 7/2016 |
| WO | 2011160430 A1 | 12/2011 |
| (Continued) | | |

OTHER PUBLICATIONS

International Search Report and Written Opinion in International Application No. PCT/US2020/038867, mailed Sep. 14, 2020 (14 pages).

(Continued)

*Primary Examiner* — Kathryn Elizabeth Limbaugh
(74) *Attorney, Agent, or Firm* — Nixon Peabody LLP

(57) ABSTRACT

A microfluidic device comprises a cell flow layer and a control layer. The cell flow layer includes a growth channel, a collection channel, a plurality of bridge channels connecting the growth channel and the collection channel, a plurality of bridge valve portions, and a plurality of cell growth trenches coupled to the growth channel. The growth channel includes an inlet valve portion and an outlet valve portion controlling flow into and out of the growth channel. The collection channel includes an inlet valve portion and an outlet valve controlling flow into and out of the collection channel. The bridge valve portions control flow between the growth channel and the collection channel. The control layer includes a first control channel actuating the bridge valve portions and a second control channel actuating the inlet (Continued)

valve portions and the outlet valve portions of the growth channel and the collection channel.

20 Claims, 12 Drawing Sheets

(56) References Cited

U.S. PATENT DOCUMENTS

| | | | |
|---|---|---|---|
| 8,691,164 B2 | 4/2014 | Butler | |
| 9,149,806 B2 | 10/2015 | Collins | |
| 2015/0247790 A1 | 9/2015 | Okumus et al. | |
| 2019/0271634 A1 | 9/2019 | Handique | |
| 2019/0344270 A1* | 11/2019 | Yoon | B01L 3/502738 |
| 2020/0264205 A1* | 8/2020 | West | G01N 15/1484 |

FOREIGN PATENT DOCUMENTS

| | | |
|---|---|---|
| WO | 2013019491 A1 | 2/2017 |
| WO | 2018140302 A1 | 8/2018 |

OTHER PUBLICATIONS

Betz, J. L., "Cloning and characterization of several dominant-negative and tight-binding mutants of lac repressor," Gene 42, pp. 283-292 (1986).
Betz, J. L et al., "Base substitution mutants of the lac operator: in vivo and in vitro affinities for lac repressor," Gene 50, pp. 123-132 (1986).
Berens, C. et al., "The role of the N terminus in Tet repressor for tet operator binding determined by a mutational analysis," J. Biol. Chem., 267(3): 1945-1952 (1992).
Lu, Y. et al., "AraC protein contacts asymmetric sites in the Escherichia coli araFGH promoter," J. Biol. Chem., 267(34): 24848-24857 (1992).
Daugherty, P. S. et al., "Flow cytometric screening of cell-based libraries," J. Immunol. Methods 243, pp. 211-227 (2000).
Elowitz, M. B. & Leibler, S., "A synthetic oscillatory network of transcriptional regulators," Nature 403, pp. 335-338 (2000).
Unger, M. A. et al., "Monolithic microfabricated valves and pumps by multilayer soft lithography," Science 288, pp. 113-116 (2000).
Wang, M. M. et al., "Microfluidic sorting of mammalian cells by optical force switching," Nat. Biotechnol., 23(1): 83-87 (2005).
Lee, W. M. et al., "Construction and calibration of an optical trap on a fluorescence optical microscope," Nat. Protoc., 2(12): 3226-3238 (2007).
Stricker, J. et al., "A fast, robust and tunable synthetic gene oscillator," Nature 456, pp. 516-519 (2008).
Buchler, N. E. & Cross, F. R., "Protein sequestration generates a flexible ultrasensitive response in a genetic network," Mol. Syst. Biol. 5, 272 (2009).
Dirla, S. et al., "Constitutive mutations in the Escherichia coli AraC protein," J. Bacteriol., 191(8): 2668-2674 (2009).
Wang, P. et al., "Report Robust Growth of Escherichia coli," Curr. Biol., 20(12): 1099-1103 (2010).
Landgraf, D. et al., "Segregation of molecules at cell division reveals native protein localization," Nat. Methods, 9(5): 480-482 (2012).
Denervaud, N. et al., "A chemostat array enables the spatio-temporal analysis of the yeast proteome," Proc. Natl. Acad. Sci., 110(39): 15842-15847 (2013).
Levine, J. H. et al., "Functional roles of pulsing in genetic circuits," Science 342, pp. 1193-2000 (2013).
Norman, T. M. et al., "Memory and modularity in cell-fate decision making," Nature 503, pp. 481-486 (2013).

Schaerli, Y. & Isalan, M., "Building synthetic gene circuits from combinatorial libraries: screening and selection strategies," Mol. Biosyst., 9(7): 1559-1567 (2013).
Teng, S.-W. et al., Robust Circadian Oscillations in Growing Cyanobacteria Require Transcriptional Feedback. Science 340, pp. 737-740 (2013).
Brewster, R. C. et al., "The Transcription Factor Titration Effect Dictates Level of Gene Expression," Cell 156, pp. 1312-1323 (2014).
Espah Borujeni, A et al., "Translation rate is controlled by coupled trade-offs between site accessibility, selective RNA unfolding and sliding at upstream standby sites," Nucleic Acids Res. 42, pp. 2646-2659 (2014).
Madsen, M. H. et al., "Accounting for PDMS shrinkage when replicating structures," J. Micromechanics Microengineering 24, 127002 (2014).
Spivey, E. C. et al., "3D-Printed Microfluidic Microdissector for High-Throughput Studies of Cellular Aging," Anal. Chem. 86, pp. 7406-7412 (2014).
Seemann, T., "Snippy: rapid haploid variant calling and core SNP phylogeny," (2015).
Taheri-Araghi, S. et al., "Cell-Size Control and Homeostasis in Bacteria," Curr. Biol. 25, pp. 385-391 (2015).
Han, Y. et al., "Review: imaging technologies for flow cytometry," Lab Chip, 16(24): 4639-4647 (2016).
Pearl Mizrahi, S. et al., "Persistence to anti-cancer treatments in the stationary to proliferating transition," Cell Cycle, 15(24): 3442-3453 (2016).
Potvin-Trottier, L. et al., "Synchronous long-term oscillations in a synthetic gene circuit," Nature 538, pp. 514-517 (2016).
Bergmiller, T. et al., "Biased partitioning of the multidrug efflux pump AcrAB-TolC underlies long-lived phenotypic heterogeneity," Science 356, pp. 311-315 (2017).
Emanuel, G. et al., "High-throughput, image-based screening of pooled genetic-variant libraries," Nat. Methods, 14(12): 1159-1162 (2017).
Lawson, M. J. et al., "In situ genotyping of a pooled strain library after characterizing complex phenotypes," Mol Syst Biol., 13(941): 1-10, (2017).
Li, Y. et al., "Multigenerational silencing dynamics control cell aging," Proc. Natl. Acad. Sci., 114(42): 11253-11258 (2017).
Lugagne, J.-B. et al., "Balancing a genetic toggle switch by real-time feedback control and periodic forcing," Nat. Commun., 8(1671): 1-9 (2017).
Okumus, B. et al., "Single-cell microscopy of suspension cultures using a microfluidics-assisted cell screening platform," Nat. Protoc., 13(1): 170-194 (2017).
Yuan, A. H. & Hochschild, A., "A bacterial global regulator forms a prion," Science 355, pp. 198-201 (2017).
Balleza, E. et al., "Systematic characterization of maturation time of fluorescent proteins in living cells," Nat. Methods, 15(1): 47-51 (2018).
Bashor, C. J. & Collins, J. J., "Understanding Biological Regulation Through Synthetic Biology," Annu. Rev. Biophys. 47, pp. 399-423 (2018).
Kaiser, M. et al., "Monitoring single-cell gene regulation under dynamically controllable conditions with integrated microfluidics and software," Nat. Commun., 9(212): 1-17 (2018).
Park, J. et al., "Molecular Time Sharing through Dynamic Pulsing in Single Cells," Cell Syst. 6, 216-229.e15 (2018).
Riglar, D. T. et al., "Variability of bacterial behavior in the mammalian gut captured using a growth-linked single-cell synthetic gene oscillator," bioRxiv 472720 (2018). doi: 10.1101/472720.
Robert, L. et al., "Mutation dynamics and fitness effects followed in single cells," Science 359, pp. 1283-1286 (2018).
Schmitz, J. et al., "Heterogeneity Studies of Mammalian Cells for Bioproduction: From Tools to Application," Trends Biotechnol., 37(6): 645-660 (2019).

* cited by examiner

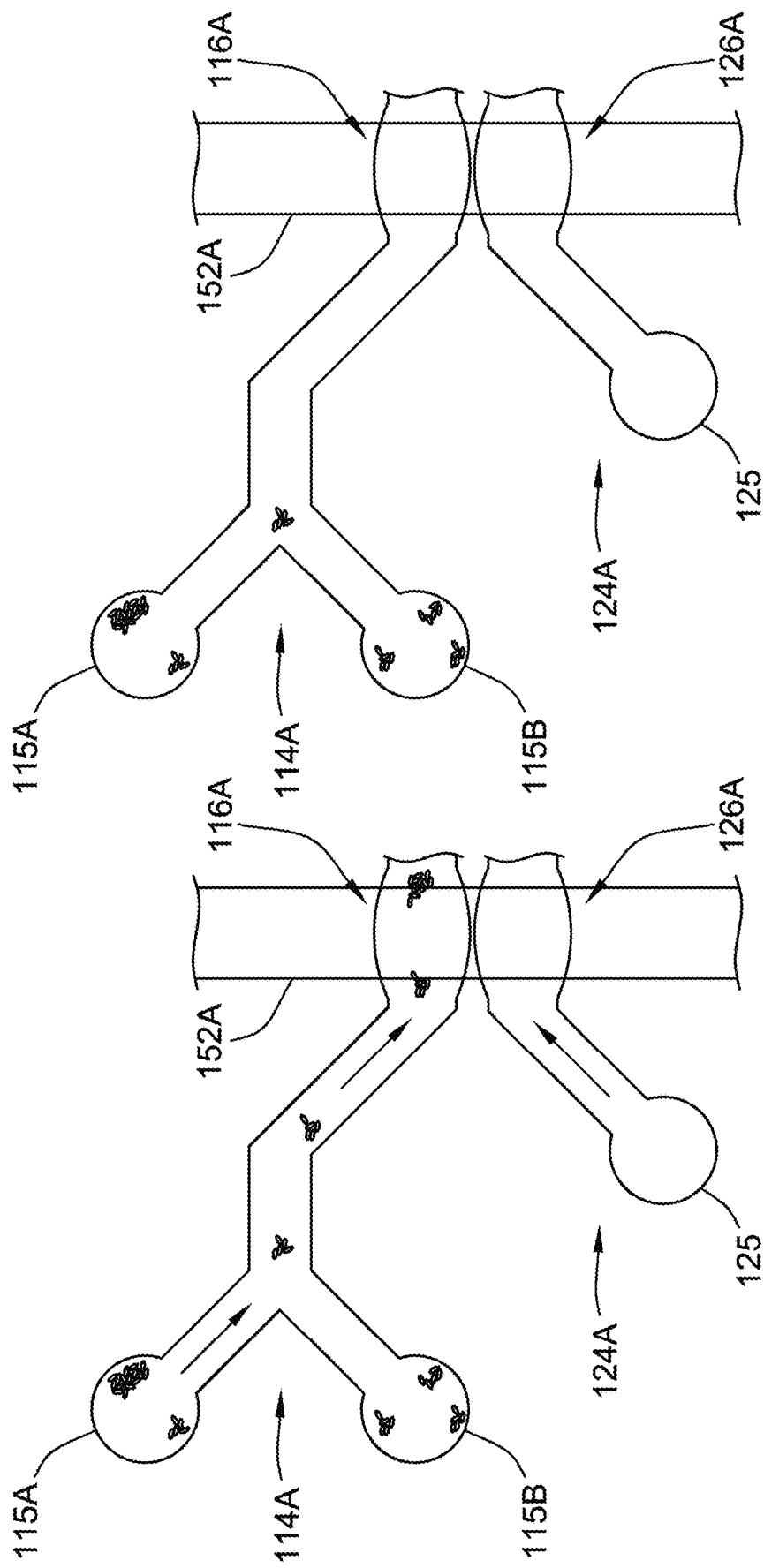

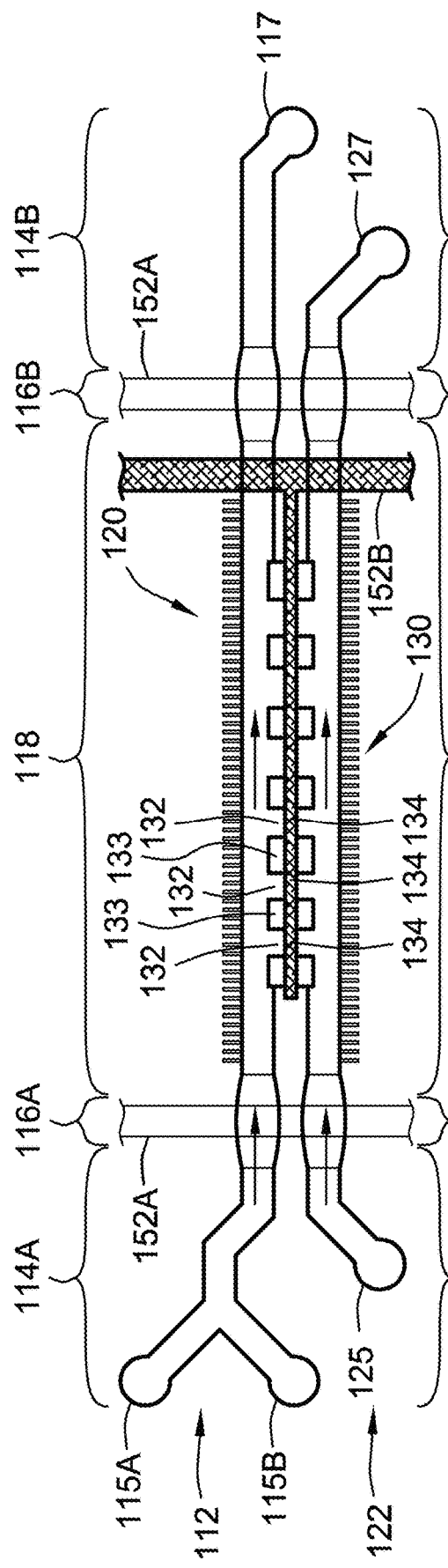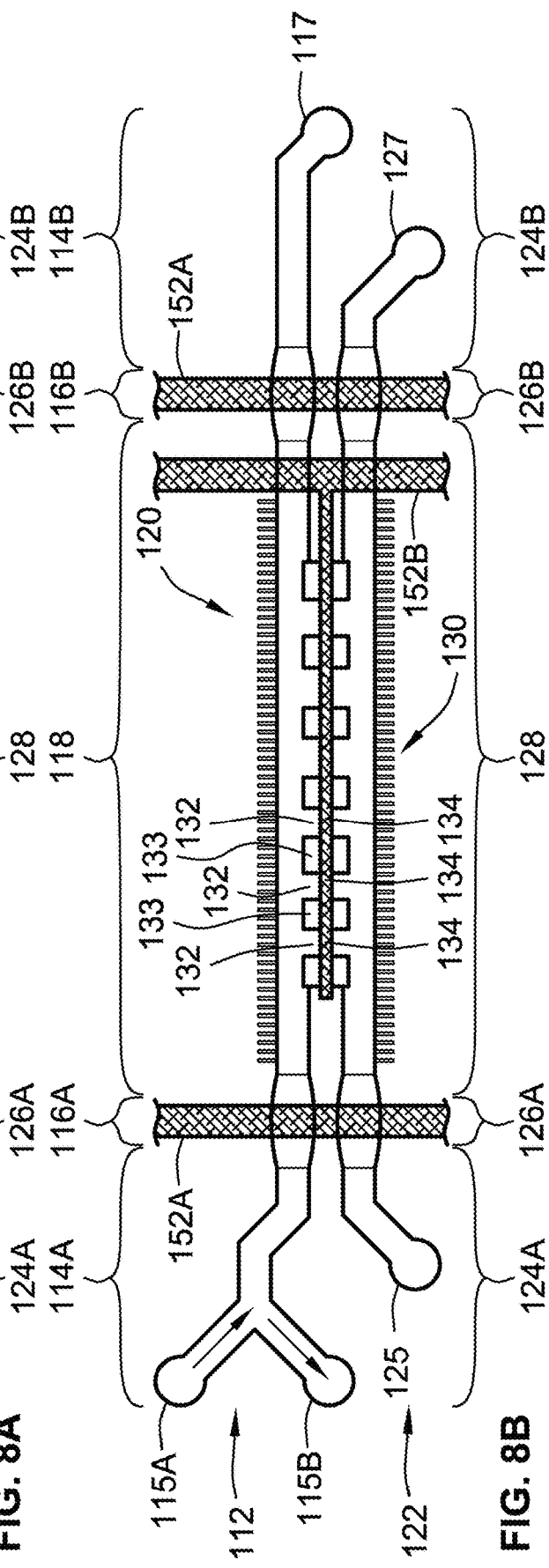

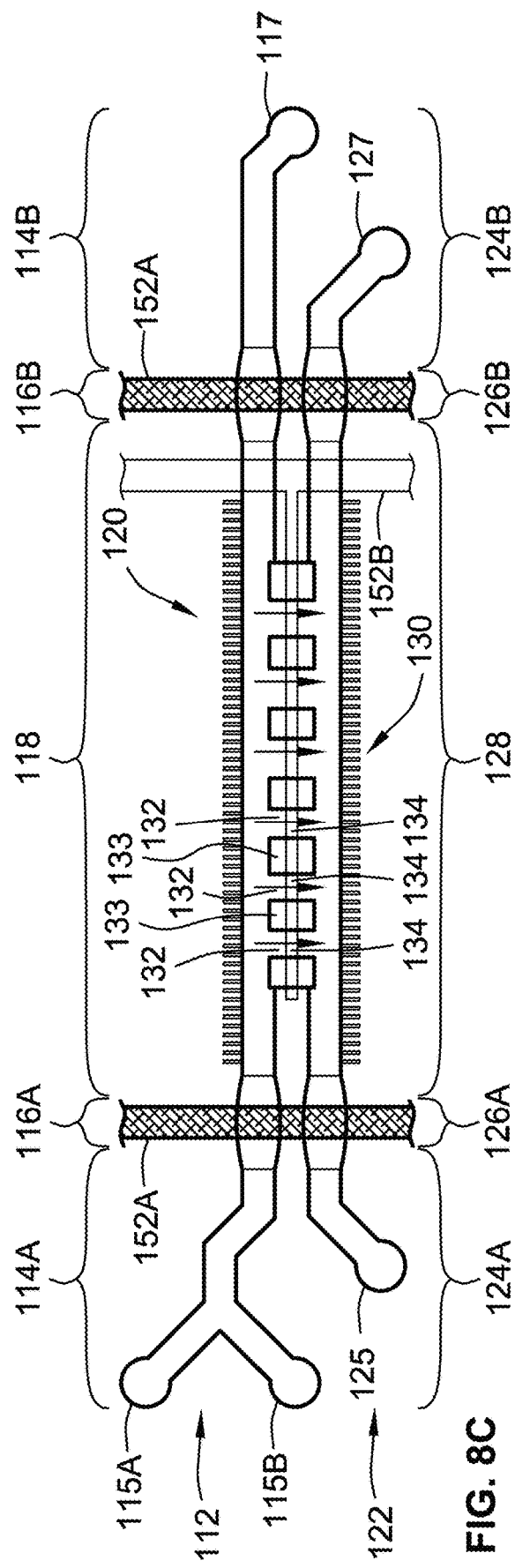

ISOLATING LIVE CELLS AFTER HIGH-THROUGHPUT, LONG-TERM, TIME-LAPSE MICROSCOPY

CROSS-REFERENCE TO RELATED APPLICATIONS

This application is a US National Stage of International Application No. PCT/US2020/038867, filed Jun. 22, 2020, which claims the benefit of and priority to U.S. Provisional Patent Application Ser. No. 62/864,091, filed on Jun. 20, 2019, entitled "ISOLATING LIVE CELLS AFTER HIGH-THROUGHPUT, LONG-TERM, TIME-LAPSE MICROSCOPY," each of which is hereby incorporated by reference herein in its entirety.

STATEMENT REGARDING FEDERALLY SPONSORED RESEARCH OR DEVELOPMENT

This invention was made with Government support under 1615487 awarded by the National Science Foundation (NSF), and under HR0011-16-2-0049 awarded by the U.S. Department of Defense/Defense Advanced Research Projects Agency. The Government has certain rights in the invention.

TECHNICAL FIELD

The present disclosure relates to microfluidic devices. Specifically, the present disclosure relates to a microfluidic device that enables long-term monitoring of cell populations and efficient extraction of cells of interest.

BACKGROUND

Genetic screens play a fundamental role in biology by identifying which genes or parts of genes determine phenotypic properties. Their power depends on the breadth of the mutant libraries that can be considered, the types of properties that can be measured, the ability to control growth conditions while ensuring spatiotemporal uniformity, and— because many mutations only change the distribution of phenotypes—on how reliably those distributions are sampled for each mutant.

Current techniques only provide endpoint low-resolution snapshots, and offer little information about growth, intracellular dynamics, and responses to environmental changes. Furthermore, because each cell is probed only once, current techniques struggle to distinguish genetically stable properties from transient phenotypic heterogeneity. Thus, new devices and methods for imaging and analyzing cells are needed.

SUMMARY

A microfluidic device for use in analyzing cells and extracting one or more cells of interest comprises a substrate; a cell flow layer coupled to the substrate; and a control layer coupled to the cell flow layer. The cell flow layer included a growth channel, a plurality of cell growth trenches, a collection channel, and a plurality of bridge channels. The growth channel has an inlet portion, an outlet portion, a main portion, an inlet valve portion, and an outlet valve portion. The inlet valve portion of the growth channel is configured to aid in selectively controlling flow between the inlet portion of the growth channel and the main portion of the growth channel. The outlet valve portion of the growth channel is configured to aid in selectively controlling flow between the main portion of the growth channel and the outlet portion of the growth channel. The plurality of cell growth trenches is fluidly coupled to the main portion of the growth channel. The collection channel has an inlet portion, an outlet portion, a main portion an inlet valve portion, and an outlet valve portion. The inlet valve portion of the collection channel is configured to aid in selectively controlling flow between the inlet portion of the collection channel and the main portion of the collection channel. The outlet valve portion of the collection channel is configured to aid in selectively controlling flow between the main portion of the collection channel and the outlet portion of the collection channel. Each of the plurality of bridge channels couples the main portion of the growth channel with the main portion of the collection channel. Each of the plurality of bridge channels includes a bridge valve portion configured to aid in selectively controlling flow between the growth channel and the collection channel. The control layer is configured to aid in actuating (i) the bridge valve portion of each of the plurality of bridge channels, (ii) the inlet valve portion of the growth channel, (iii) the outlet valve portion of the growth channel, (iv) the inlet valve portion of the collection channel, and (v) the outlet valve portion of the collection channel.

A method of analyzing cells and extracting one or more cells of interest using a microfluidic device having a growth channel, a plurality of cell growth trenches fluidly coupled to the growth channel, and a collection channel fluidly coupled to the growth channel comprises: injecting one or more cells and growth media into an inlet portion of the growth channel such that the one or more cells and the growth media flow into the main portion of the growth channel and fill at least one of the plurality of cell growth trenches; closing an inlet valve portion of the growth channel and an outlet valve portion of the growth channel; cleaning the inlet portion of the growth channel to remove contaminants from the inlet portion of the growth channel; analyzing the one or more cells in the at least one of the plurality of cell growth trenches to identify the one or more cells of interest; opening the plurality of bridge valve portions allow fluid to flow through the plurality of bridge channels between the main portion of the growth channel and the main portion of the collection channel; causing the one or more cells of interest to move from the at least one of the plurality of cell growth trenches, through the main portion of the growth channel and one or more of the plurality of bridge channels, into a main portion of the collection channel; closing the plurality of bridge valve portions; opening an inlet valve portion of the collection channel and an outlet valve portion of the collection channel; causing the one or more cells of interest to move from the main portion of the collection channel into an outlet portion of the collection channel; and collecting the one or more cells of interest from the outlet portion of the collection channel.

The above summary is not intended to represent each implementation or every aspect of the present disclosure. Additional features and benefits of the present disclosure are apparent from the detailed description and figures set forth below.

BRIEF DESCRIPTION OF THE DRAWINGS

The disclosure will be better understood from the following description of example implementations together with reference to the accompanying drawings.

FIG. 4A is a top view of an inlet portion of the example microfluidic device of FIG. 1A during injection of cells and growth media, according to aspects of the present disclosure;

FIG. 4B is a top view of the inlet portion of FIG. 4A after injection of cells and growth media, according to aspects of the present disclosure;

FIG. 8A is a top view of a growth channel and a collection of the example microfluidic device of FIG. 1A as cells and growth media are injected into the growth channel, according to aspects of the present disclosure;

FIG. 8B is a top view of the growth channel and the collection channel of FIG. 8A as an inlet portion of the growth channel is cleaned, according to aspects of the present disclosure; and FIG. 8C is a top view of the growth channel and the collection channel of FIG. 8A as cells are moved from the growth channel to the collection channel, according to aspects of the present disclosure.

Figure 1A:
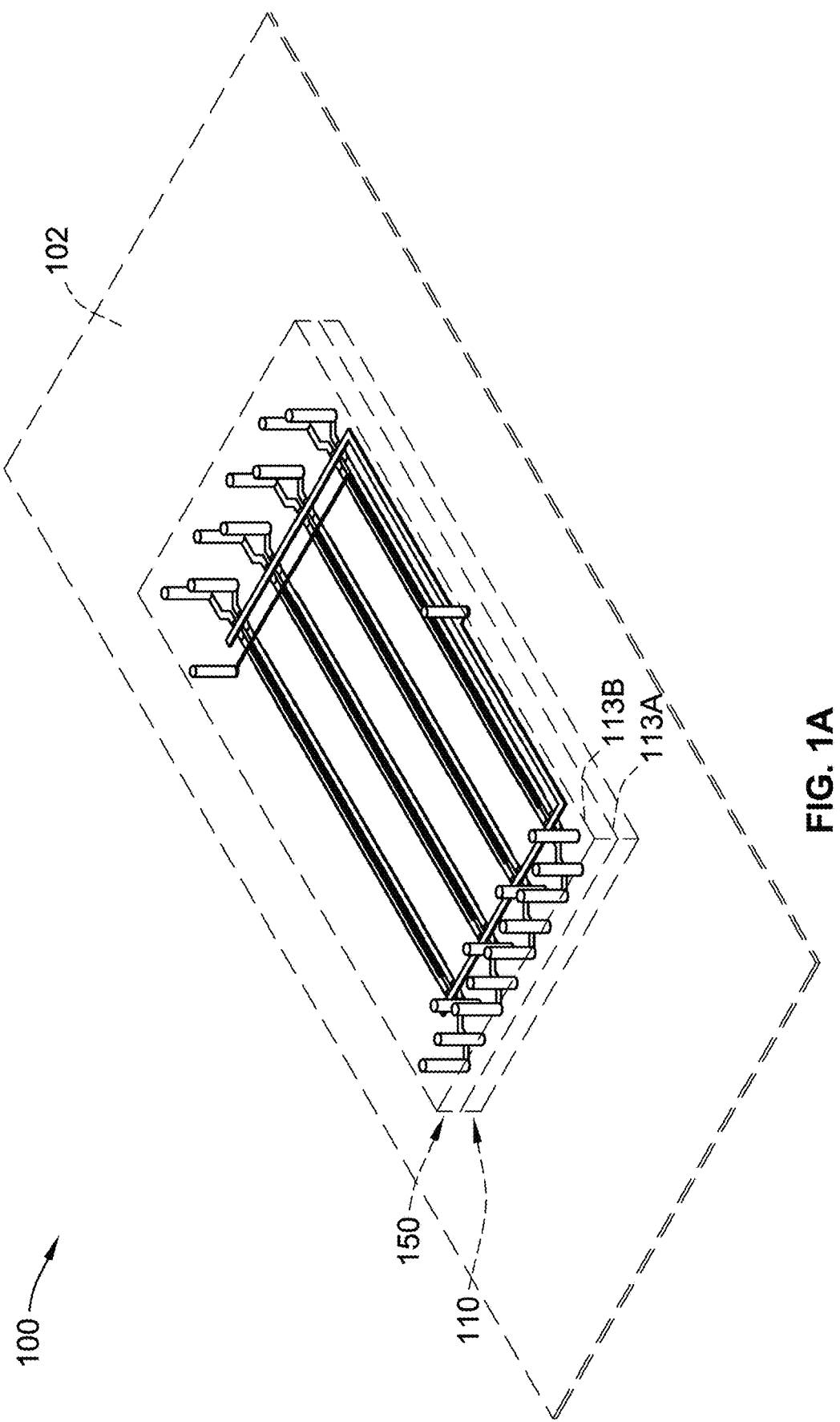
FIG. 1A is a perspective view of an example microfluidic device for analyzing cells and extracting one or more cells of interest, according to aspects of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

While the present disclosure is susceptible of many different forms, there is shown in the drawings and will herein be described in detail example implementations of the present disclosure, with the understanding that the present disclosure is to be considered as an example of the principles of the present disclosure and is not intended to limit the broad aspect of the present disclosure to the illustrated implementations.

Figure 1B:
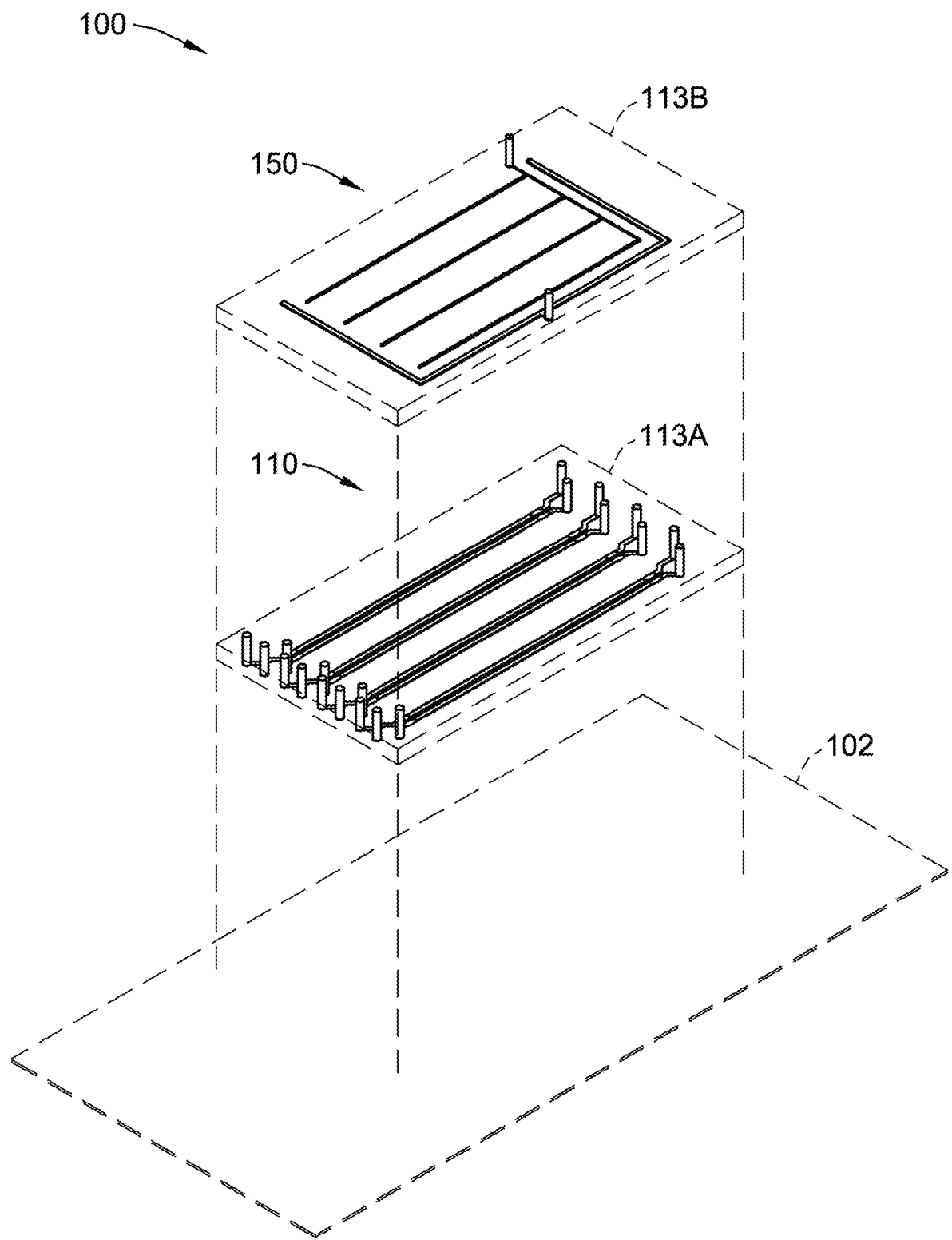
FIG. 1B is an exploded view of the example microfluidic device of FIG. 1A, according to aspects of the present disclosure.

FIG. 1A shows a perspective view of a microfluidic device 100 that can be used to analyze cells, and extract one or more cells of interest. FIG. 1B shows an exploded view of the microfluidic device 100. In some implementations, device 100 is used for multigenerational time-lapse microscopy. In these implementations, isogenic populations of cells can be confined and grown within the device 100, which allows for the cells to be imaged over many generations. One or more cells of interest can then be extracted from the device 100, for use in a variety of downstream applications.

The device 100 includes a coverslip 102, a cell flow layer 110 coupled to the coverslip, and a control layer 150 coupled to the cell flow layer 110. Generally, the cell flow layer 110 is mounted above the coverslip 102, and the control layer 150 is mounted above the cell flow layer 110. The cell flow layer 110 includes a variety of different channels through which cells (and other fluids such as growth media and cleaning fluids or solutions) can flow during use. The control layer 150 can include different channel that are filled with a fluid in order to actuate various different valves of the cell flow layer 110. As discussed in more detail herein, the valves can be actuated to selectively control the flow of cells and other fluids through the various channels of the cell flow layer 110.

In some implementations, the cell flow layer 110 and the control layer 150 are both comprised of blocks of polydimethylsolixane (PDMS) and are cast from separate molds. In some implementations, the coverslip 102 is made from glass. The various channels of the cell flow layer 110 and the control layer 150 can be formed using any suitable fabrication technique(s). In some implementations, the cell flow layer 110 and the control layer 150 are fabricated using multilayer soft lithography. In these implementations, molds are initially formed from silicon wafers using UV lithography techniques. The PDMS layers are then cast by flowing liquid PDMS into the silicon molds, and then subsequently cured so that the PDMS hardens. The two PDMS layers can be bonded together (for example via curing or partial curing), and bonded to the coverslip 102 (for example via plasma bonding), and then further baked. Thus, the negative space of the channels of the cell flow layer 110 and the control layer 150 are imprinted from the positive silicon wafer molds.

The result of the fabrication process is the three-dimensional device 100. In some implementations, the cell flow layer 110 and the control layer 150 have a length of between about 20.0 mm and about 40.0 mm, or about 30.0 mm; the cell flow layer 110 and the control layer 150 have a width of between about 10.0 mm and about 20.00 mm, or about 17.0 mm; the cell flow layer 110 has a height of between about 40.0 μm and about 60.0 μm, or about 50.0 μm; and the control layer 150 has a height of between about 2.0 mm and about 10.0 mm, or about 6.0 mm.

The various channels of the cell flow layer 110 are defined on an underside of the cell flow layer 110. The cell flow layer 110 thus includes an upper wall 113A that forms the upper wall (e.g., the ceiling) of the various channels defined in the cell flow layer 110. When the cell flow layer 110 is bonded to the coverslip 102, the coverslip 102 forms a lower wall (e.g., a floor) of the various channels of the cell flow layer 110. Similarly, the various channels of the control layer 150 are defined on an underside of the control layer 150. An upper wall 113B of the control layer 150 forms an upper wall (e.g., a ceiling) of the various channels of the control layer 150. The upper wall 113A of the cell flow layer 110 forms a lower wall (e.g., a floor) of the various channels of the control layer 150. The channels of the cell flow layer 110 and the control layer 150 are each fluidly coupled to the atmosphere via a plurality of vertical channels extending upward through the cell flow layer 110 and/or the control layer 150, and a plurality of openings defined in the upper wall of the control layer 150.

Figure 2A:
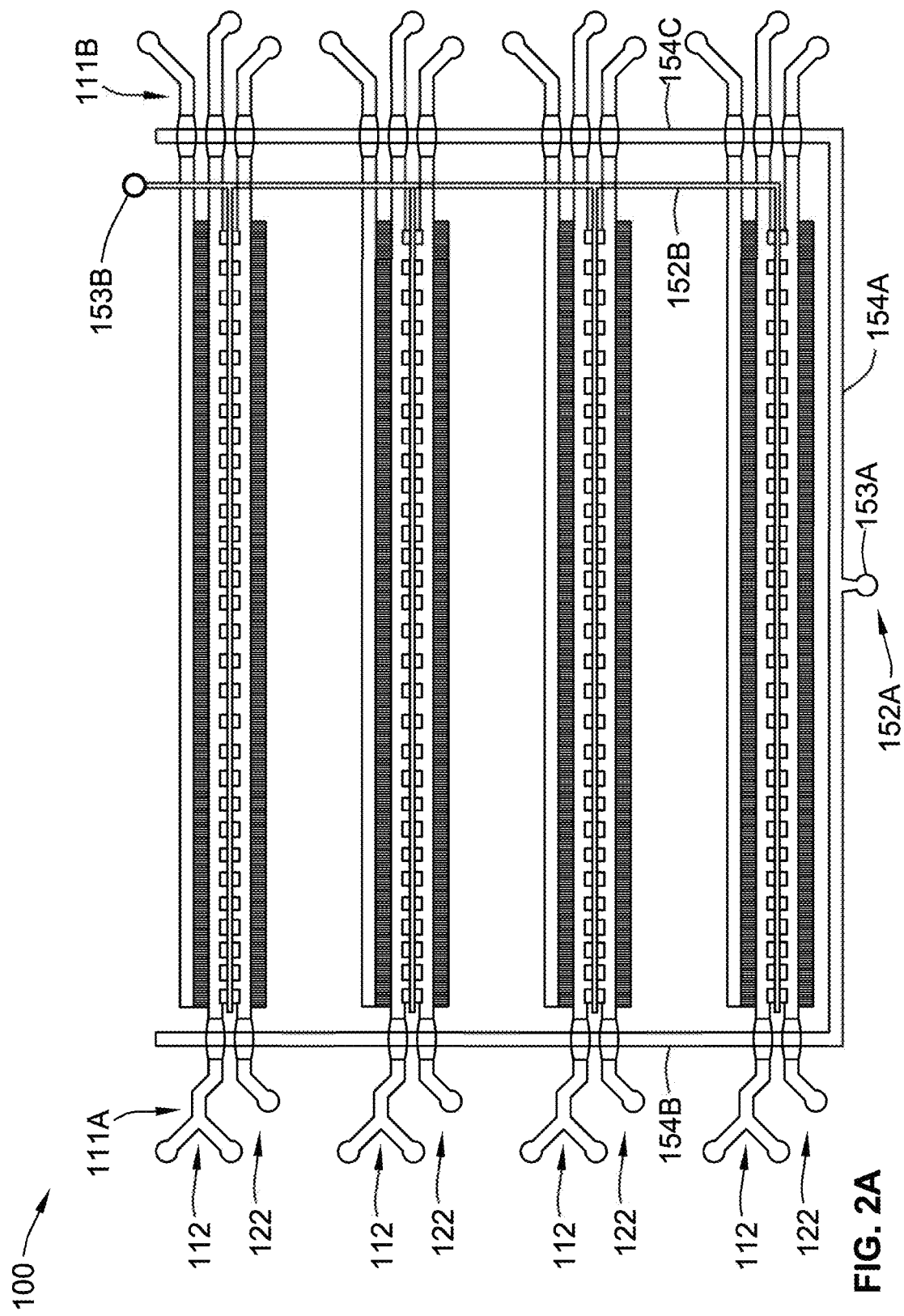
FIG. 2A is a top view of the layout of channels of the example microfluidic device of FIG. 1A, according to aspects of the present disclosure.
Figure 2B:
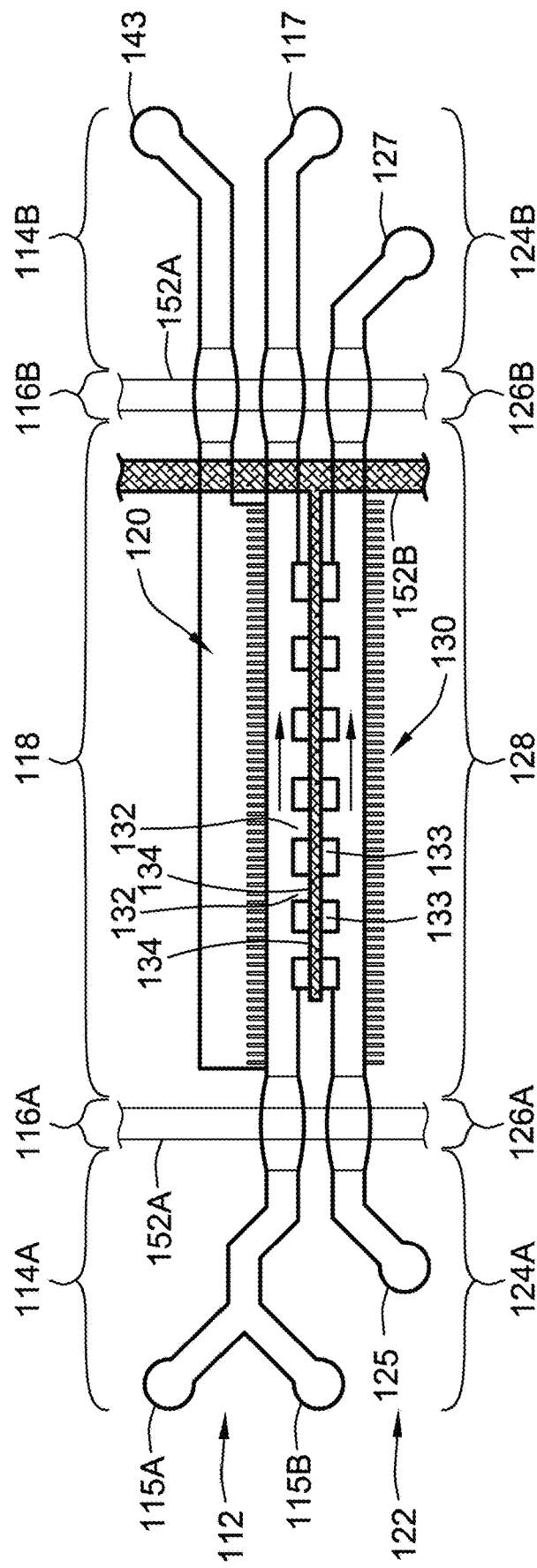
FIG. 2B is a zoomed-in view of a portion of the layout of channels of FIG. 2A, according to aspects of the present disclosure.

FIG. 2A is a top view of the device 100 that shows a two-dimensional layout of the various channels of the cell flow layer 110 and the control layer 150. FIG. 2B is a zoomed-in top view of the device 100 that shows one set of growth and collection channels. The cell flow layer 110 includes four pairs of analysis channels. Each pair of analysis channels includes a growth channel 112 and a collection channel 122. While any monitoring and imaging processes are taking place during use of the device 100, cells are generally located in the growth channel 112. Once a cell of interest is identified, the cell of interest can be moved to the collection channel 122, from which it can be collected. Generally, any one or more of the pairs of the growth channel 112 and the collection channel 122 can be used during operation of the device 100. For example, all four pairs can be used simultaneously to analyze the same types of cells; all four pairs can be used simultaneously to analyze different types of cells; fewer than all four pairs can be used simultaneously to analyze the same or different types of cells. While the device 100 is shown in FIG. 2A as having four pairs of growth channels 112 and collection channels 122, the device 100 can have any number of growth channels 112 and collection channels 122, including one or more.

The growth channel 112 is formed from different portions, and includes an inlet portion 114A, an inlet valve portion 116A, a main portion 118, an outlet valve portion 116B, and an outlet portion 114B. The different portions of the growth channel 112 are located at different positions along the length of the cell flow layer 110. For example, the inlet portion 114A and the inlet valve portion 116A are located at a first end 111A of the cell flow layer 110, while the outlet valve portion 116B and the outlet portion 114B are located at a second end 111B of the cell flow layer 110. The main portion 118 is located between the first end 111A and the second end 111B. Generally, each portion of the growth channel 112 is a channel through which cells and fluid can flow.

The cell flow layer 110 further includes a plurality of cell growth trenches 120 that are fluidly coupled to at least the main portion 118 of the growth channel 112. The cell growth trenches 120 are positioned on a first side of the growth channel 112, and are configured to extend from the growth channel 112 in a direction that is perpendicular to the direction in which the growth channel 112 extends between the first end 111A of the device 100 and the second end 111B of the device 100.

The cell growth trenches 120 are configured to be filled with cells during use of the device 100. The cell growth trenches 120 have a width that is generally equal to or slightly larger than the width of the cells that are being analyzed during use of the device 100. Thus, the cells in any one of the cell growth trenches 120 are arranged in a linear, one-dimensional grouping (e.g., the cells are geometrically constrained to a single-file line). As cells that initially fill the cell growth trenches 120 begin to divide, the cells eventually fill the dead-end cell growth trenches 120 with an isogenic lineage of cells. These cells generally have the same genetic makeup, and are arranged in a single one-dimensional line. The length of the cell growth trenches 120 (e.g., the distance that the cell growth trenches 120 extend from the growth channel 112) can be between about 1.0 μm and about 100.0 μm. The width of the cell growth trenches 120 can be between about 0.1 μm and about 50.0 μm. The height of the cell growth trenches 120 can be between about 0.1 μm and about 50.0 μm. Generally, the dimensions of the cell growth trenches 120 can be adjusted during the wafer fabrication process depending on the required sensitivity of microscopy (e.g., cell growth trenches more closely spaced apart will have greater between-trench signal spillover, for example due to point-spread function of light, than cell growth trenches positioned farther apart), the size of the cells to be used with the device 100, throughput demands, etc. The distance between adjacent pair of cell growth trenches 120 can be between about 0.1 μm and about 10.0 μm.

The collection channel 122 is positioned on a second side of the growth channel 112, opposite the cell growth trenches 120. Thus, the growth channel 112 is positioned between the cell growth trenches 120 and the collection channel 122. The collection channel 122 also extends between the first end 111A of the device 100 and the second end 111B of the device 100 in a direction that is parallel to the growth channel 112 and perpendicular to the cell growth trenches 120. Similar to the growth channel 112, the collection channel 122 includes an inlet portion 124A, an inlet valve portion 126A, a main portion 128, an outlet valve portion 126B, and an outlet portion 124B. The different portions of the collection channel 122 are located at different positions along the length of the cell flow layer 110. For example, the inlet portion 124A and the inlet valve portion 126A are located at the first end 111A of the cell flow layer 110, while the outlet valve portion 126B and the outlet portion 124B are located at the second end 111B of the cell flow layer 110. The main portion 128 is located between the first end 111A and the second end 111B. Generally, each portion of the collection channel 122 is a channel through which cells and fluid can flow.

In the illustrated implementation, the cell flow layer can also include a plurality of cell growth trenches 130 fluidly coupled to the main portion 128 of the collection channel 122. The cell growth trenches 130 are positioned on a side of the collection channel 122 opposite from the growth channel 112. The cell growth trenches 130 are configured to extend from the collection channel 122 in a direction that is perpendicular to the direction in which the collection channel 122 extends between the first end 111A of the device 100 and the second end 111B of the device 100. Generally, the cell growth trenches 130 can have the same or similar dimensions as the cell growth trenches 120.

The cell flow layer 110 further includes a plurality of bridge channels 132 positioned between the growth channel 112 and the collection channel 122. The bridge channels 132 are open spaces defined between adjacent pairs of bridge protrusions 133, which generally extend the entire height of the cell flow layer 110 to the upper wall of the cell flow layer 110. In some implementations, the bridge channels 132 are located only between the main portion 118 of the growth channel 112 and the main portion 128 of the collection channel 122. In other implementations, the bridge channels 132 can extend further such that the cell flow layer 110 includes bridge channels 132 located between other portions of the growth channel 112 and the collection channel 122. The bridge channels 132 are configured to allow cells and fluid to flow between the growth channel 112 and the collection channel 122. The bridge channels 132 each have a length of about 200.0 µm, and a width of between about 50.0 µm and about 100.0 µm.

As noted herein, the growth channel 112 includes an inlet valve portion 116A and an outlet valve portion 116B, and the collection channel 122 includes an inlet valve portion 126A and an outlet valve portion 126B. These valve portions can be actuated to aid in selectively controlling the flow of cells and fluid through the growth channel 112 and the collection channel 122. The inlet valve portion 116A of the growth channel 112 controls flow between the inlet portion 114A of the growth channel 112 and the main portion 118 of the growth channel 112. The inlet valve portion 126A of the collection channel 122 controls flow between the inlet portion 124A of the collection channel 122 and the main portion 128 of the collection channel 122. The outlet valve portion 116B of the growth channel 112 controls flow between the main portion 118 of the growth channel 112 and the outlet portion 114B of the growth channel 112. The outlet valve portion 126B of the collection channel 122 controls flow between the main portion 128 of the collection channel 122 and the outlet portion 124B of the collection channel 122.

In the illustrated implementations, the valve portions 116A, 116B, 126A, 126B of the growth channel 112 and the collection channel 122 are formed at least partially by portions of the upper wall of the cell flow layer 110. Because the upper wall of the cell flow layer 110 forms the upper wall of the growth channel 112 and the collection channel 122, the valve portions 116A, 116B, 126A, 126B are in turn formed at least partially by portions of the upper walls of the growth channel 112 and the collection channel 122 themselves. When the valve portions 116A, 116B, 126A, 126B are actuated, the upper walls of the valve portions 116A, 116B, 126A, 126B are compressed downward toward the coverslip 102 in order to close off the growth channel 112 and the collection channel 122 at the valve portions 116A, 116B, 126A, 126B. When the valve portions 116A, 116B, 126A, 126B are compressed and the channels of the cell flow layer 110 are closed off to prevent fluid flow, the valve portions 116A, 116B, 126A, 126B are in an open state. When the valve portions 116A, 116B, 126A, 126B are uncompressed and the channels of the cell flow layer 110 are opened to allow fluid flow, the valve portions 116A, 116B, 126A, 126B are in a closed state.

The inlet valve portion 116A of the growth channel 112 is located between the inlet portion 114A and the main portion 118. Thus, when the upper wall of the inlet valve portion 116A is compressed downward, the portion of the upper wall of the growth channel 112 between the inlet portion 114A and the main portion 118 is compressed downward, to prevent cells and fluid from flowing in the growth channel 112 between the inlet portion 114A and the main portion 118. The inlet valve portion 126A of the collection channel 122 is located between the inlet portion 124A and the main portion 128. Thus, when the upper wall of the inlet valve portion 126A is compressed downward, the portion of the upper wall of the collection channel 122 between the inlet portion 124A and the main portion 128 is compressed downward, to prevent cells and fluid from flowing in the collection channel 122 between the inlet portion 124A and the main portion 128.

The outlet valve portion 116B of the growth channel 112 is located between the main portion 118 and the outlet portion 114B. Thus, when the upper wall of the outlet valve portion 116B is compressed downward, the portion of the upper wall of the growth channel 112 between the main portion 118 and the outlet portion 114B is compressed downward, to prevent cells and fluid from flowing in the growth channel 112 between the main portion 118 and the outlet portion 114B. The outlet valve portion 126A of the collection channel 122 is located between the main portion 128 and the outlet portion 124B. Thus, when the upper wall of the outlet valve portion 126B is compressed downward, the portion of the upper wall of the collection channel 122 between the main portion 128 and the outlet portion 124B is compressed downward, to prevent cells and fluid from flowing in the collection channel 122 between the main portion 128 and the outlet portion 124B.

The cell flow layer 110 also includes a plurality of bridge valve portions 134 that are configured to aid in selectively controlling flow through the bridge channels 132. Thus, the bridge valve portions 134 can be actuated to prevent cells and fluid from flowing between the growth channel 112 and the collection channel 122. Similar to valve portions 116A, 116B, 126A, and 126B, the bridge valve portions 134 are formed at least partially by portions of the upper wall of the cell flow layer 110. Because the upper wall of the cell flow layer 110 forms the upper walls of the bridge channels 132, the bridge valve portions 134 are in turn formed at least partially by portions of the upper walls of the bridge channels 132 themselves. When the bridge valve portions 134 are actuated, at least a portion of the upper walls of the bridge channels 132 are compressed downward toward the coverslip 102, in order to close off the bridge channels 132.

The bridge valve portions 134 overlap at least partially with the bridge channels 132, because the bridge valve portions 134 are portions of the upper walls of the bridge channels 132 that can be compressed downward. In order to prevent cell and fluid flow through the bridge channels 132, the entire width of the upper wall of each bridge channel 132 (between adjacent bridge protrusions 133) forms the respective bridge valve portions 134. Thus, when the bridge valve portions 134 are actuated, the entire width of the upper walls of the bridge channels 132 compress downward to block the bridge channels 132.

In some implementations, the bridge valve portions 134 extend along the entire length of the bridge channels 132 between the growth channel 112 and the collection channel 122. In these implementations, the entire upper wall of each bridge channel 132 forms a bridge valve portion 134. In other implementations, the bridge valve portions 134 extend along only a portion of the length of the bridge channels 132 between the growth channel 112 and the collection channel 122. In these implementations, only a portion of the upper wall of each bridge channel 132 forms a bridge valve portion 134. However, because the bridge valve portions 134 still extend across the entire width of the bridge channels 132 between adjacent pairs of bridge protrusions 133, the bridge valve portions 134 are still able to control flow through the bridge channels 132.

Generally, each bridge valve portion 134 is configured to control the flow of cells and fluids through one or more of the bridge channels 132. In some implementations, each bridge valve portion 134 controls flow through a respective one of the bridge channels 132. In other implementations, at least one of the bridge valve portions 134 controls the flow through two or more of the bridge channels 132.

The control layer 150 includes one or more control channels that can be pressurized in order to actuate the various valve portions of the cell flow layer 110. The control channels of the control layer 150 overlap with the portions of the upper wall of the cell flow layer 110 that form the various valve portions of the cell flow layer 110. When the control channels are pressurized, the upper walls of the valve portions compress downward to move to their closed state, and the control channels expand. The control channels can then be depressurized to return the valve portions to their open states, and the control channels contract.

In the illustrated implementation, the control layer 150 defines a first control channel 152A and a second control channel 152B. The first control channel 152A is configured to control all of the inlet valve portions 116A and 126A, and all of the outlet valve portions 116B and 126B. The second control channel 152B is configured to control all of the bridge valve portions 134. Thus, the first control channel 152A extends within the control layer 150 such that the first control channel 152A overlaps with portions of the upper wall of the cell flow layer 110 that form the upper wall of all of the inlet valve portions 116A and 126A, and all of the outlet valve portions 116B and 126B. In the illustrated implementation, the first control channel 152A can have a U shape. A base 154A of the U shape extends between the first end 111A and the second 111B of the cell flow layer 110. One of the legs 154B of the U shape extends across all of the inlet portions 114A of the growth channels 112, and all of the inlet portions 124A of the collection channels 122. Similarly, the other leg 154C of the U shape extends across all of the outlet portions 114B of the growth channels 112, and all of the outlet portions 124B of the collection channels 122. In other implementations, the first control channel 152A can have other shapes and/or configurations, so long as the first control channel 152A overlaps with all of the required valve portions of the cell flow layer 110.

The second control channel 152B also extends within the control layer 150 such that the second control channel 152B overlaps with portions of the upper wall of the cell flow layer 110 that form the upper wall of all of the bridge valve portions 134. In the illustrated implementations, the second control channel 152B includes a first portion 158A, a second portion 158B, and a third portion 158C. Portion 158A overlaps with all of bridge valve portions 134 of the top pair of growth and collection channels 112, 122. Portion 158B overlaps with all of bridge valve portions 134 of the middle pair of growth and collection channels 112, 122. Portion 158C overlaps with all of bridge valve portions 134 of the bottom pair of growth and collection channels 112, 122. The second control channel 152B also includes a first intermediate portion 160A connecting the first portion 158A and the second portion 158B; and a second intermediate portion 160B connecting the second portion 158B and the third portion 158C. In other implementations, the second control channel 152B can have other shapes and/or configurations, so long as the second control channel 152B overlaps with all of the required valve portions of the cell flow layer 110.

Figure 3A:
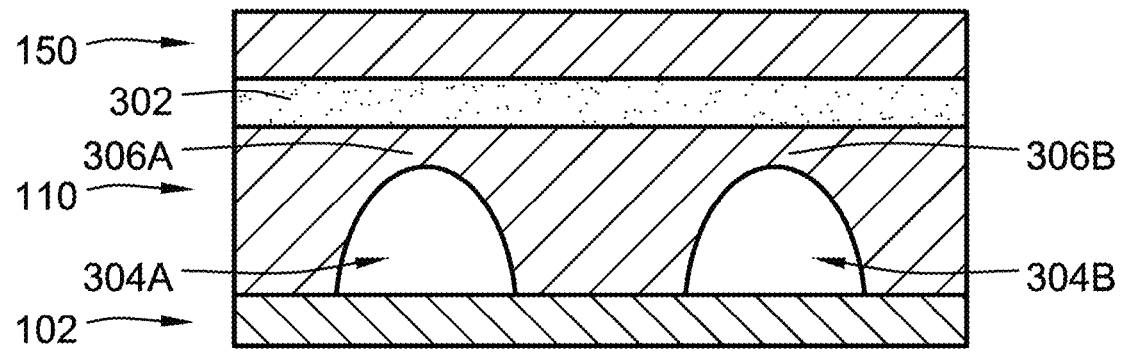
FIG. 3A is a cross-sectional view of two valve portions of the example microfluidic device of FIG. 1A in an open state, according to aspects of the present disclosure.
Figure 3B:
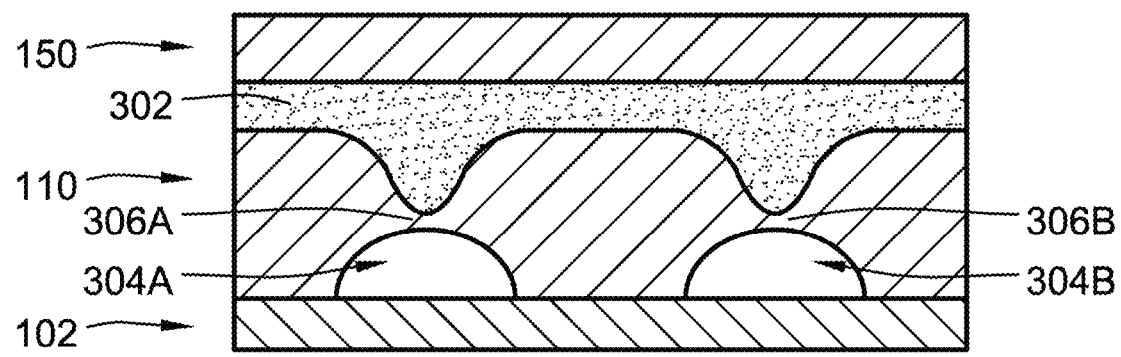
FIG. 3B is a cross-sectional view of the two valve portions of FIG. 3A moving from the open state to a closed state, according to aspects of the present disclosure.
Figure 3C:
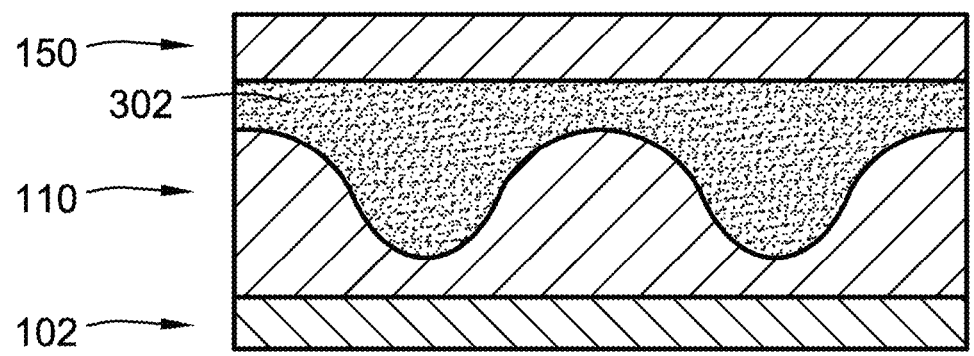
FIG. 3C is a cross-sectional view of the two valve portions of FIG. 3A in the closed state, according to aspects of the present disclosure.

FIGS. 3A-3C show a cross-sectional view of an example control channel 302 of the control layer 150 being pressurized, to actuate two example valve portions 304A and 304B of the cell flow layer 110 and close off the underlying channels. The two example valve portions 304A, 304B could be the inlet valve portions 116A and 126A, the two outlet valve portions 116B and 126B, or two adjacent bridge valve portions 134. In FIG. 3A, the control channel 302 is filled with an incompressible or substantially incompressible fluid, such as distilled water. In FIG. 3A, the control channel 302 is filled the fluid, but has not yet been pressurized. Thus, the upper walls 306A and 306B of the valve portions 304A and 304B are not compressed, and the valve portions 304A and 304B are in their open state.

In FIG. 3B, the fluid in the control channel 302 has begun to be pressurized (e.g., pressure has been applied to the control channel 302). Thus, the upper walls 306A and 306B of the valve portions 304A and 304B have begun to compress and move toward the coverslip 102. The valve portions 304A and 304B are not fully closed, and thus fluid can still flow through the valve portions 304A and 304B. In FIG. 3C, more pressure is applied to the control channel 302, such that the upper walls 306A and 306B of the valve portions 304A and 304B compress down to the coverslip 102. When this compression occurs, the valve portions 304A and 304B are moved to their closed states, such that no fluid is able to flow through the valve portions 304A and 304B. To return the valve portions 304A and 304B to their open states, the pressure is removed from the control channel 302. The material forming the upper walls 306A and 306B (which can be PDMS in some implementations) is generally elastic, such that the upper walls 306A and 306B return to their uncompressed states (FIG. 3A) when the pressure is removed from the control channel 302.

As shown in FIG. 3A, the valve portions 304A and 304B generally have a dome-shaped cross-section, and the thickness of the upper wall of the cell flow layer 110 at the valve portions 304A and 304B is relatively thinner than the thickness of the upper wall of the cell flow layer 110 at different locations. Because the thickness of the upper wall at the valve portions 304A and 304B is thin, the upper wall is flexible and can compress as shown in FIGS. 3B and 3C. Further, the dome-shaped cross-section aids in ensuring that the upper wall at the valve portions 304A and 304B compresses, and does not resist the pressure from the control channel 302. Thus, the cross-sections of the inlet valve portions 116A, 126A; the outlet valve portions 116B, 126B; and the bridge valve portions 134 are all dome-shaped. These locations also have a relatively thinner upper wall than at other locations within of the growth channel 112, the collection channel 122, and the bridge channels 132, to aid in enabling the upper walls of the valve portions to compress. At locations in the growth channel 112, the collection channel 122, and the bridge channels 132 that do not have a valve portion, the upper wall is relative thicker, and channels have a generally square or rectangular cross-section.

Referring back to FIGS. 2A and 2B, in order to actuate the valve portions 116A, 116B, 126A, and 126B, the first control channel 152A is pressurized, such that the upper walls of the valve portions 116A, 116B, 126A, and 126B are compressed to the coverslip 102 and no fluid can flow through the valve portions 116A, 116B, 126A, and 126B. Removal of pressure from the first control channel 152A returns the valve portions 116A, 116B, 126A, and 126B to their open states, such that fluid can again flow through the valve portions 116A, 116B, 126A, and 126B. Similarly, in order to actuate the bridge valve portions 134, the second control channel 152B is pressurized, such that the upper walls of the bridge valve portions 134 are compressed to the coverslip 102 and no fluid can flow through the bridge valve portions 134. Removal of pressure from the second control channel 152B returns the bridge valve portions 134 to their open states, such that fluid can again flow through the bridge channels 132. In some implementations, the first control channel 152A and 152B are always filled with the incompressible fluid during use (whether the valve portions remain open or closed), and pressure can be applied to the filled control channels 152A, 152B to actuate the valves. In these implementations, all of the valve portions controlled by each control channel can be actuated simultaneously or near simultaneously. In other implementations, the incompressible fluid is partially or wholly removed from the control channels 152A, 152B when the valve portions are returned to their open states.

Referring back to FIGS. 2A and 2B, in some implementations, the cell flow layer 110 can include a plurality of back channels 142 that are positioned adjacent to the cell growth trenches 120, such that each set of cell growth trenches 120 is positioned between one of growth channels 112 and one of the back channels 142. Each of the cell growth trenches 120 can be open to one of the back channels 142. Generally, the opening in each cell growth trench 120 is sufficiently narrow so that growth media and other fluids can flow through the openings into the back channels 142, but the cells populating the cell growth trenches 120 cannot pass through the opening. The back channels 142 can be used to populate the cell growth trenches 120 with cells, as discussed further herein.

The various channels of the cell flow layer 110 and the control layer 150 include openings through which fluid can flow into and out of. In some implementations, the inlet portion 114A of the growth channels 112 includes a first inlet opening 115A and a second inlet opening 115B, as shown in the top two growth channels 112 in FIG. 2A. In other implementations, the inlet portion 114A of the growth channels 112 includes only the first inlet opening 115A, as shown in the bottom growth channel 112. The inlet portion 124A of each collection channel 122 includes an inlet opening 125. In some implementations, the inlet portions 114A can have three or more inlet openings. In some implementations, the inlet portions 124A can have two or more inlet openings.

The outlet portions similarly include outlet openings through which fluid can flow into or out of. The outlet portions 114B of the growth channels 112 each include an outlet opening 117. The outlet portions 124B of the collection channels 122 each include an outlet opening 127. The first control channel 152A and the second control channel 152B each inlet an opening via which the control channels 152A, 152B can be filled with fluid and pressurized. The first control channel 152A includes an opening 153A, and the second control channel 152B includes an opening 153B. The back channels 142 adjacent to each set of cell growth trenches 120 each include a back channel outlet opening 143.

The various inlet openings, outlet openings, and control channel openings are generally all three dimensional, and rise vertically up to the upper wall of the control layer 150, as shown in FIGS. 1A and 1B. Various devices, mechanisms, etc. can be connected to the openings in the upper wall of the control layer 150 in order to inject cells, fluid, etc. into the openings. In some example, pumps (such as peristaltic pumps, syringe pumps, pressure tubes, etc.) can be coupled to the openings in order to inject cells, growth media, cleaning fluids, etc., and to pressurize and depressurize the control channels 152A and 152B (via a flowed incompressible fluid). In the illustrated implementation, the back channel outlet opening 143 is open to the atmosphere exterior to the device 100. However, in other implementations, the back channel outlet opening 143 can be positioned entirely within the cell flow layer 110, and can fluidly couple the back channel 142 to the main portion 118 of the growth channel 112.

Figure 4C:
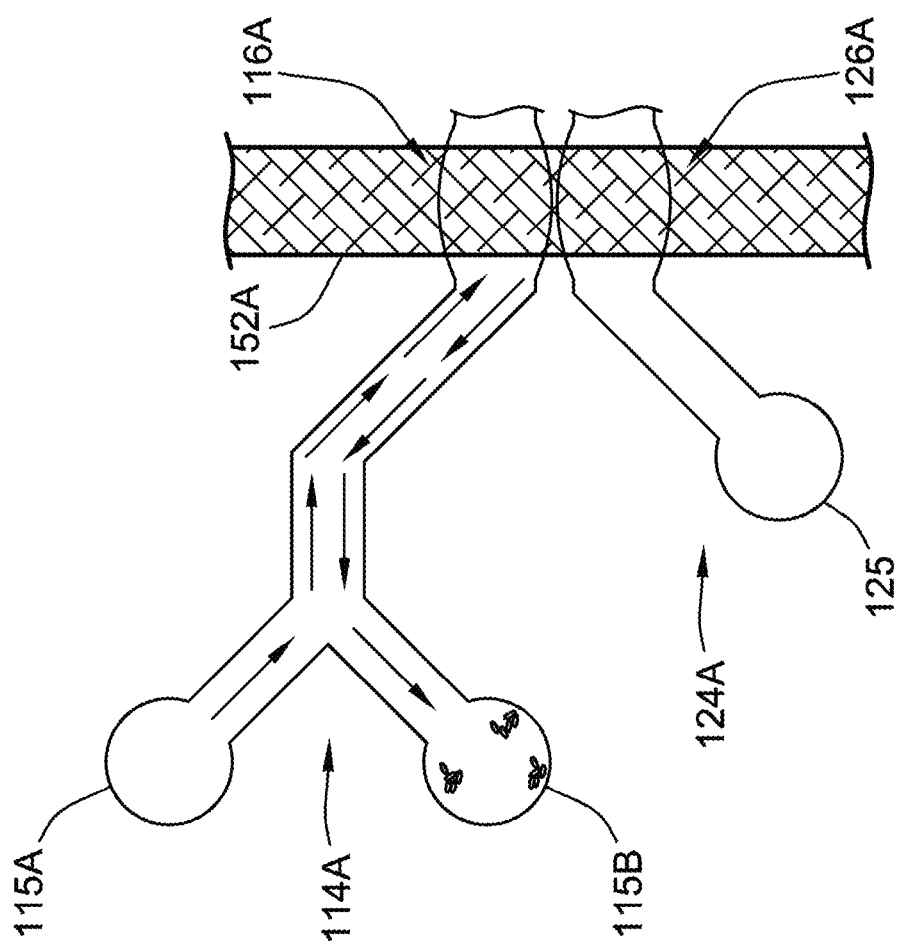
FIG. 4C is a top view of the inlet portion of FIG. 4A being cleaned to remove residual contaminants, according to aspects of the present disclosure.

Referring now to FIGS. 4A-4C, the inlet portions 114A of the growth channels 112 can be cleaned using the two inlet openings 115A and 115B. As shown in FIG. 4A, one or both of the inlet openings 115A, 115B can be used to inject cells and growth media into the main portion 118 of the growth channel 112. The first control channel 152A is not pressurized, and thus the inlet valve portion 116A of the growth channel 112 is in its open state. Cells, growth media, or other substances injected into the first inlet opening 115A are able to flow into the main portion 118 of the growth channel 112. Afterwards, a certain amount of material may remain in the inlet portion 114A (e.g., biofilms, cells tightly lodges within cracks and/or crevices in the PDMS that cannot be removed by forceful flushing of growth media or displaced by cell growth), as shown in FIG. 4B. During use of the device 100, the inlet valve portion 116A generally remains in an open state, and thus this excess material needs to be removed from the inlet portion 114A, so as to not contaminate the growth channel 112 with excess cells and debris during use of the device 100.

As shown in FIG. 4C, the first control channel 152A can be pressurized in order to close the inlet valve portion 116A of the growth channel 112. With the inlet valve portion 116A closed, any fluid injected into the inlet portion 114A cannot flow through the inlet valve portion 116A and into the main portion 118. Then, a cleaning fluid can be injected into the first inlet opening 115A. Because the inlet valve portion 116A is closed and the inlet portion 114A includes a second inlet opening 115B, the cleaning fluid can flow through the inlet portion 114A and exit at the second inlet opening 115B. The cleaning fluid can remove the excess cells and other material from the inlet portion 114A, so that the inlet valve portion 116A can be in the open state during use of the device 100 without contaminating the growth channel 112.

A variety of different types of fluids can be used to clean the inlet portion 114A. In some implementations, the cleaning fluid is undiluted bleach. In some implementations, the cleaning fluid is diluted bleach (such as 10% (v/v) bleach). In some implementations, a multi-stage cleaning process involving multiple different cleaning fluids can be used. For example, the inlet portion 114A can first be cleaned using bleach (diluted or undiluted) or another strong cleaning fluid to remove any material remaining in the inlet portion 114A. Next, ethanol (which could be diluted (10% (v/v/)) or undiluted) is injected into the inlet portion 114A to remove excess bleach from the inlet portion 114A. Finally, growth media is injected into the inlet portion 114A to remove excess ethanol and restore nutrient balance. In some implementations, water is used instead of ethanol.

This multi-stage cleaning process can be beneficial, as in many applications of the device 100, growth media is flowed (injected, pumped, etc.) into the growth channel 112 during use. Thus, the multi-stage cleaning process is able to (1) utilize strong cleaning fluids such as bleach to ensure that all excess cells and other material is removed, and (2) ensure that no excess or residual bleach remains in the inlet portion 114A after cleaning, so that no bleach is inadvertently flowed into the growth channel 112 during use.

Figure 5A:
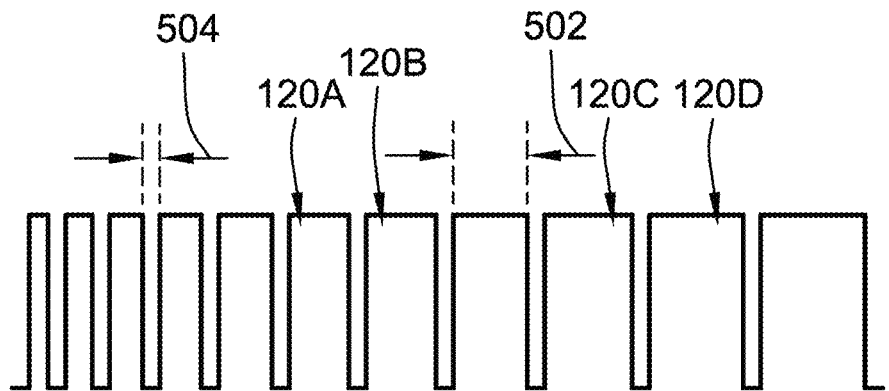
FIG. 5A is a top view of cell growth trenches of the example microfluidic device of FIG. 1A, according to aspects of the present disclosure.
Figure 5B:
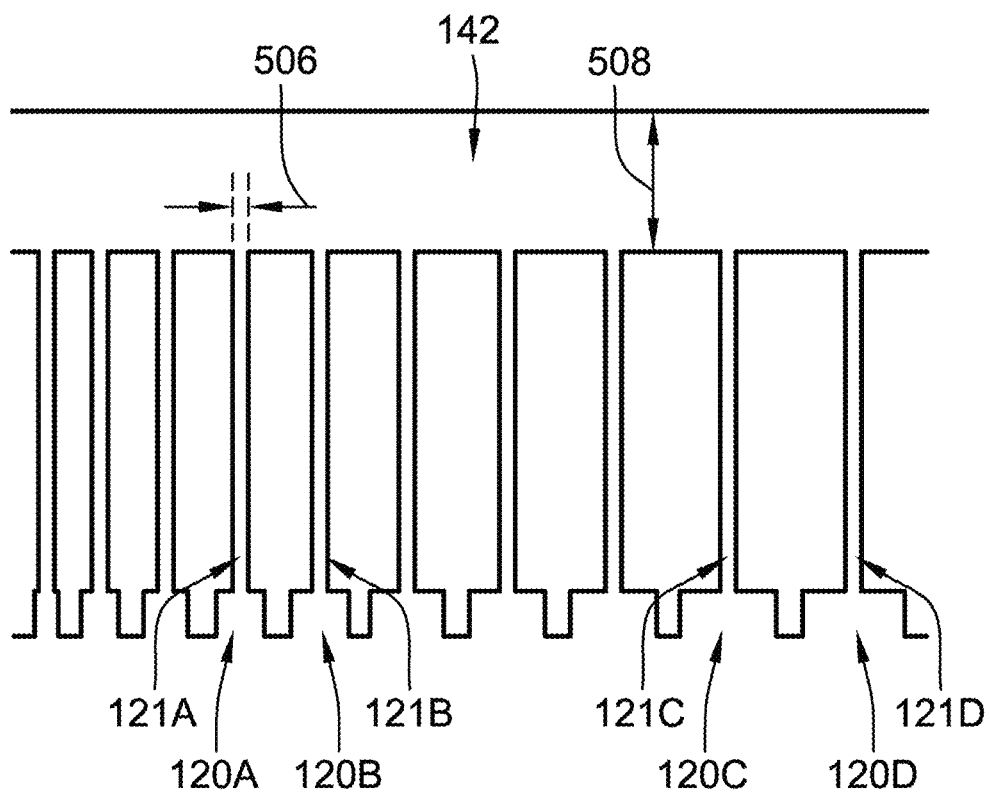
FIG. 5B is a top view of cell growth trenches of the example microfluidic device of FIG. 1A coupled to a back channel, according to aspects of the present disclosure.

FIGS. 5A and 5B illustrates various dimensions of the cell growth trenches and the back channels. The width 502 of each of the cell growth trenches is between about 0.1 µm and about 50.0 µm. The height of each of the cell growth trenches is between about 0.1 µm and about 50.0 µm. Different cell growth trenches extending from the same growth channel can have different widths. For example, FIG. 5A shows a plurality of cell growth trenches, including cell growth trenches 120A, 120B, 120C, and 120D. Trench 120A has the smallest width of these four trenches, which increase in size through 120B, 120C, and 120D. In general, the cell growth trenches can have any desired width, depending on the application. Adjacent pairs of cell growth trenches are spaced apart a distance 504. This distance can be between about 0.1 µm and about 20.0 µm.

FIG. 5B shows a series of cell growth trenches (including cell growth trenches 120A, 120B, 120C, and 120D) that are open at their back end to a back channel 142. Cell growth trench 120A includes an opening 121A. Cell growth trench 120B includes an opening 121B. Cell growth trench 120C includes an opening 121C. Cell growth trench 120D includes an opening 121D. Each of these openings 121A-121D can have a width 506 that is between about 1.0 µm and about 300.0 µm, and a height of between about 0.1 µm and about 20.0 µm. The back channel 142 can have a width 508 that is between about 1.0 µm and about 300.0 µm, and a height of between about 0.1 µm and about 50.0 µm.

Figure 6:
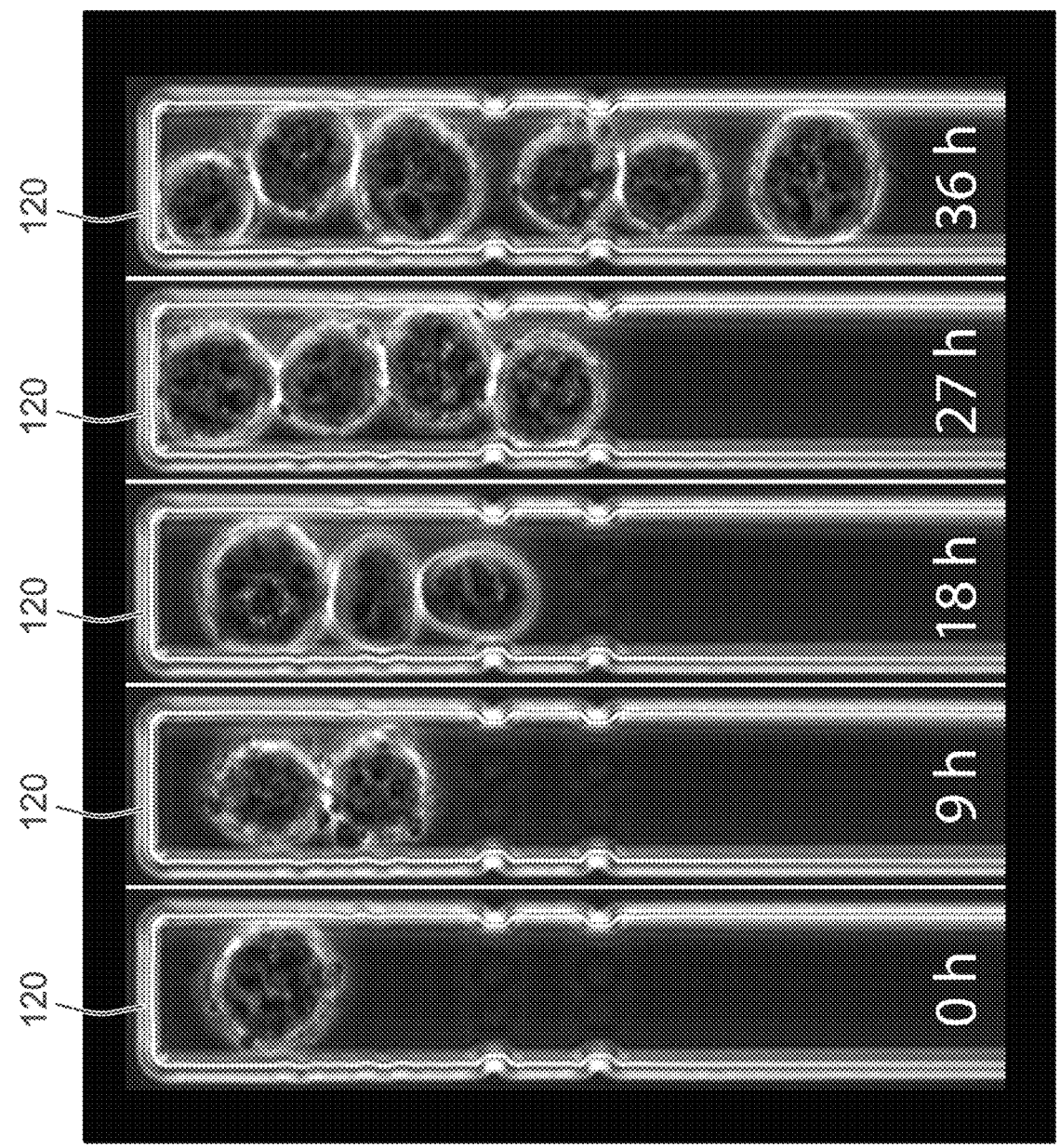
FIG. 6 is a kymograph showing the growth of cells in a cell growth trench, according to aspects of the present disclosure.

FIG. 6 illustrates a time series of one of the cell growth trenches 120, showing the growth of an isogenic lineage of a single starting cell. At zero hours, cell growth trench 120 includes a single cell. After nine hours, the single cell has grown to two cells. At eighteen hours, the cell growth trench 120 contains three cells. At twenty-seven hours, the cell growth trench 120 contains four cells. Finally, at thirty-six hours, the cell growth trench 120 contains six cells. As demonstrated in FIG. 6, the narrow cell growth trenches 120 enable the cell population to grow in a linear one-dimensional grouping, e.g., in a single-file line within the cell growth trench 120. This one-dimensional grouping enables the individual cells to be imaged, analyzed, monitored, etc., and also aids in tracking the lineage of the cells.

As shown in FIG. 6, as the cell population grows, cells start getting pushed closer to the end of the cell growth trench 120 nearest the growth channel 112. Once the cell growth trench 120 is full, the next division will push the last cell out into the growth channel 112. The cell population grows at a rate of $2^n$, where n is the number of cell generations. Generally, the cell growth trenches 120 are long enough to contain between about five cells and about ten cells, and an isogenic lineage can be achieved in between about two and about ten generations of growth. Because the isogenic lineage is achieved so quickly, robustly, and passively through cell growth, the cell growth trenches 120 do not need to be individually loaded with single cells or multiple cells from the same lineage (e.g., pooled mixed-family populations may be randomly seed within cell trenches, as discussed further herein).

Figure 7:
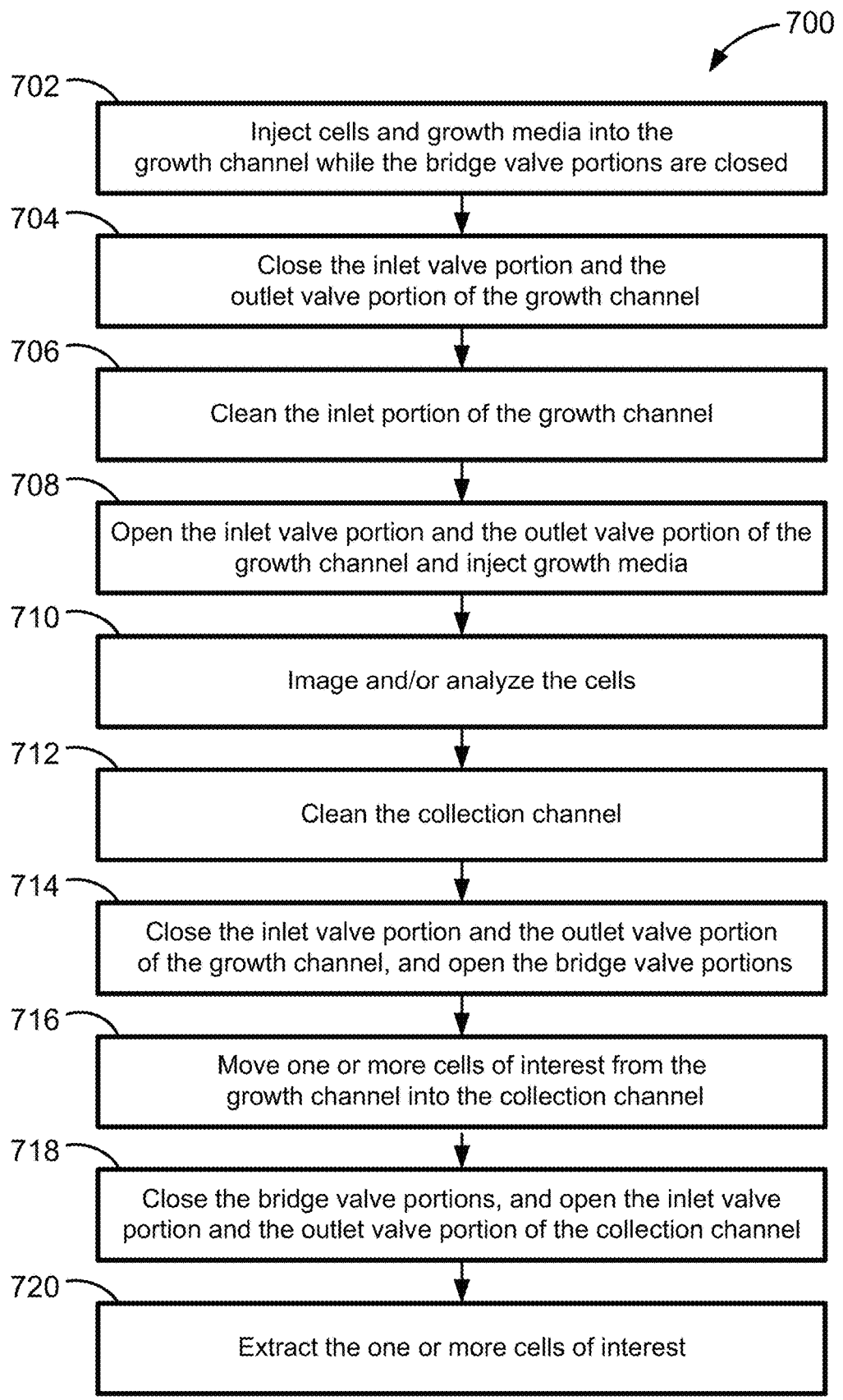
FIG. 7 is a flowchart of a method for analyzing cells and extracting one or more cells of interest, according to aspects of the present disclosure.

FIG. 7 illustrates a flowchart of a method 700 for using the device 100. FIGS. 8A-8C illustrate the stages of the device 100 at different steps of method 700. At step 702, cells and growth media are injected into the growth channel 112 through the inlet portion 114A. The cells and growth media can be injected via one or both of the inlet openings 115A and 115B. The cells and growth media are injected while the bridge valve portions 134 are closed. As shown in FIG. 8A, the first control channel 152A is unpressurized, so that the inlet valve portions 116A and 126A are open. The cells and growth media are thus able to flow through the inlet valve portion 116A into the main portion 118 of the growth channel 112. The bridge valve portions 134 are closed, so that the cells and growth media do not flow through the bridge channels 132 to the collection channel 122.

At step 704, the inlet valve portions 116A, 126A and the outlet valve portions 116B, 126B are closed, by pressurizing the first control channel 152A. As shown in FIG. 8B, when the first control channel 152A is pressurized, the inlet valve portions 116A, 126A and the outlet valve portions 116B, 126B move to a closed state. When these valve portions are in their closed states, the cells and the growth media remain in the main portion 118 of the growth channel 112, and are prevented from flowing into the inlet portion 114A or the outlet portion 114B. The bridge valve portions 134 remain closed, so that the cells and the growth media cannot flow through the bridge channels 132.

At step 706, the inlet portion 114A is cleaned by injecting a cleaning fluid into either the first inlet opening 115A or the second inlet opening 115B. As shown in FIG. 8B, because the first control channel 152A is pressurized and the inlet valve portion 116A is closed, the cleaning fluid flows through the inlet portion 114A between the two inlet openings 115A and 115B. The cleaning fluid thus removes contaminants such as residual cells, growth media, bacteria, etc. In some implementations, cleaning the inlet portion 114A include using a three-stage process, as described herein. In these implementations, bleach is first flowed through the inlet portion 114A to remove the contaminants. Ethanol can then be flowed through the inlet portion 114A to remove excess bleach, and finally growth media can be flowed through the inlet portion 114A to remove excess ethanol and restore nutrient balance. In some implementations, water is used instead of ethanol.

When the cells and the growth media are injected into the device 100, there are multiple techniques that can be used to cause the cells to populate the cell growth trenches 120. In some implementations, the cells populate the cell growth trenches 120 via diffusion. In these implementations, the inlet valve portions 116A and 126A, the outlet valve portions 116B and 126B, and the bridge valve portions 134 all remain closed. The cells in the main portion 118 of the growth channel 112 are then able to diffuse into the cell growth trenches 120. Closing the bridge valve portions 134 ensures that the cells do not inadvertently diffuse through the bridge channels 132 into the collection channel 122. Closing the inlet valve portions 116A and 126A, and the outlet valve portions 116B and 126B ensures that the cells do not inadvertently diffuse out of the main portion 118 of the growth channel 112. Closing the inlet valve portions 116A and 126A, and the outlet valve portions 116B and 126B also prevents any fluids from flowing into or out of the main portion 118 of the growth channel 112, which could slow or prevent some or all of the cells from diffusing into the cell growth trenches 120. This diffusion process can occur before, during, or after the inlet portion 1114A is cleaned, so long as the inlet valve portions 116A and 126A, and the outlet valve portions 116B and 126B are closed.

In another implementation, centrifugation can be used to load the cell growth trenches 120. This technique can be useful for dilute cultures that cannot be concentrated, and thus will have difficulty diffusing into the cell growth trenches 120. In these implementations, once the cells and the growth media are injected into the growth channel 112, the device 100 can be spun using a centrifuge or other rotating mechanism, such that the cells are caused to flow into the cell growth trenches. Because the device 100 is spinning, it is generally not possible to pressurize the first control channel 152A and the second control channel 152B, and all of the valve portions remain open during the centrifuge-based loading process. Thus, the inlet portion 114A must generally be cleaned after to using the centrifuge. The collection channel 122 also needs to be cleaned after using the centrifuge.

In implementations where the cell flow layer 110 includes a back channel 142, diverted convective flow of fluid through the cell growth trenches 120 can be used to draw cells into the cell growth trenches 120. In these implementations, the bridge valve portions 134 remain closed. The loading via diverted convective flow can occur before the inlet portion 114A is cleaned, so long as the inlet valve portions 116A and 126A, and the outlet valve portions 116B and 126B are closed during the inlet cleaning process.

Referring back to FIG. 7, once the inlet portion 114A has been cleaned, at step 708 the inlet valve portion 116A and the outlet valve portion 116B are opened, and additional growth media can be flowed into the main portion 118 of the growth channel 112. At step 710, the cells in the cell growth trenches 120 can be imaged, monitored, analyzed, etc. At this stage of method 700, the device 100 appears in the configuration illustrated in FIG. 8A. The additional growth media can be flowed into the growth channel 112 as part of causing the cells to populate the cell growth trenches 120. However, the growth media is generally continually flowed into the main portion 118 of the growth channel 112 during analysis of the cells in the cell growth trenches 120. Thus, the inlet valve portion 116A and the outlet valve portion 116B of the growth channel 112 are generally open during the analysis of the cells in the cell growth trenches 120. In other implementations however, the inlet valve portion 116A and the outlet valve portion 116B of the growth channel 112 are closed after the additional growth media is flowed into the main portion 118 of the growth channel 112. In these implementations, the imaging and/or analysis occurs while the inlet valve portion 116A and the outlet valve portion 116B of the growth channel 112 are closed.

Once the cells have populated the cell growth trenches 120, a variety of different types of analysis can take place. Cells can be imaged over time using any number of different microscopy techniques including, but not limited to, fluorescence, phase contrast, bright field, light sheet, or any type of super resolution imaging modality. To assay extracellular secretions, antibody-conjugated beads or other analyte detection systems may be flown into the main portion 118 of the growth channel 112. Additionally, oil or other fluids immiscible with water may be flown into the main portion 118 of the growth channel 112 to trap cells and aqueous media within the cell growth trenches 120, effectively generating sealed-off reaction compartments. After such extracellular agents are assayed by imaging, oil may be purged from the main portion 118 of the growth channel 112 and replaced with growth media to resume growth of all cells within the cell growth trenches 120.

At step 712, the collection channel 122 can be cleaned by flowing cleaning fluid into the collection channel 122 through the inlet opening 125. Cells of interest are eventually moved into the collection channel 122, and thus potential contaminants generally need to be removed from the collection channel 122 before the cells of interest are introduced. Cleaning the collection channel 122 generally includes the same three-stage cleaning process applied to the inlet portion 114A of the growth channel 112. A cleaning fluid (such as diluted or undiluted bleach) can first be flowed through the collection channel 122. Ethanol is then flowed through the collection channel 122 to remove residual bleach. Finally, growth media is flowed through the collection channel 122 to remove residual ethanol. In some implementations, water is used instead of ethanol.

As shown in FIG. 8A, because the second control channel 152B is pressurized and the bridge valve portions 134 are closed, the fluids used during the cleaning process flow through the entire collection channel 122 without entering the growth channel 112. The cleaning fluid removes cells and other contaminants present in the collection channel 122, as well as within any upstream and downstream connectors, tubing, etc., deposited from assembling chip in a non-sterile environment.

Cleaning of the collection channel 122 can generally occur at any point after cells have been loaded into the cell growth trenches 120. Thus, cleaning the collection channel 122 can occur during or after the imaging and/or analysis of the cells in step 710. The inlet valve portion 126A and the outlet valve portion 126B of the collection channel 122 must be closed prior to cleaning the collection channel 122.

If one or more cells of interest are identified during the monitoring and analysis stages, the one or more cells of interest can easily be extracted from the device 100 using the bridge channels 132 and the collection channel 122. At step 714, the inlet valve portions 116A and 126A, and the outlet valve portions 116B and 126B are first closed, and the bridge valve portions 134 are opened, as shown in FIG. 8C. The bridge valve portions 134 are opened after the inlet valve portions 116A and 126A, and the outlet valve portions 116B and 126B are closed, to ensure that no cells are affected by residual flow through the inlet valve portions 116A and 126A, and the outlet valve portions 116B and 126B. At step 716, the one or more cells of interest are moved from the cell growth trenches 120 into the collection channel 122. The one or more cells of interest are able to flow from the cell growth trenches 120, through the bridge channels 132, and into the main portion 128 of the collection channel 122. Because the inlet valve portions 116A, 126A and the outlet valve portions 116B, 126B are closed, the one or more cells of interest cannot inadvertently flow into the inlet portions 114A, 124A or the outlet portions 114B, 124B.

The one or more cells of interest can be moved using any suitable technique. In some implementations, electrowetting or dielectrophoresis (which can include optoelectronic tweezers) can be used. In other implementations, optical tweezers can be used. Optical tweezers are optical instruments that use focused laser beams to impart forces on small particles. In some implementations, the optical tweezers can be implemented using a laser (such as a neodymium-doped yttrium aluminum garnet laser), a beam expander, a variety of different lenses and mirrors to steer the laser beam to a desired location, and a microscope objective and condenser to form the desired beam shape and intensity profile. During use with the device 100, the components of the optical tweezers can generally be positioned in any direction relative to the device 100. The laser beam of the optical tweezers propagates into the cell flow layer 110 and traps or grabs a cell to be moved. The device 100 can be moved relative to stationary optical tweezers, and/or the laser beam of the optical tweezers can itself be steered to manipulate the trapped cell. The optical tweezers can then move the cell of interest from one of the cell growth trenches 120, through one of the bridge channels 132, and into the main portion 128 of the collection channel 122.

Closure of the inlet valve portions 116A, 126A and the outlet valve portions 116B, 126B prevents residual convective flows and minimizes drag forces on cells, and thus permitting reliable cell transport via optical tweezers at low laser powers. Additionally, an array of optical tweezers may be generated (i.e., holographic optical trapping) via implementation of beam-splitting, mode forming, and adaptive wavefront correction. Holographic optical trapping offers the benefit of being able to simultaneously transport more than one cell.

Generally, any number of cells of interest can be moved into the collection channel 122. In some implementations, a single cell of interest can be removed from a single cell growth trench 120. In other implementations, a single cell of interest can be removed from each of multiple cell growth trenches 120. In additional implementations, multiple cells of interest can be removed from a single cell growth trench 120. In still other implementations, multiple cells of interest can be removed from each of multiple cell growth trenches 120. In yet other implementations, a single cell can be removed from each of a first set of one or more cell growth trenches 120, and multiple cells can be removed from each of a second set of one or more cell growth trenches 120.

At step 718, the bridge valve portions 134 are closed, and the outlet valve portion 126B of the collection channel 122 is opened. At step 720, the one or more cells of interest are extracted from the outlet portion 124B of the collection channel 122. The one or more cells of interest can be moved from the main portion 128 of the collection channel 122 to the outlet portion 124B of the collection channel 122 using any suitable technique, such as by flowing growth media through the collection channel 122 or by using optical tweezers.

In some implementations, one or more cells of interest can be moved to the cell growth trenches 130 of the collection channel 122 after being removed from the growth channel 122. The cells of interest can be maintained and monitored in the cell growth trenches 130 before being moved to the outlet portion 124B and extracted. Depending on the type of analysis being performed, it may be beneficial to remove cells of interest from the growth channel 112 but not immediately extract the cells of interest from the collection channel 122. In these implementations, the cells of interest that are extracted from the collection channel 122 may include progeny of cells of interest moved into the cell growth trenches 130 of the collection channel 122.

In some implementations, once the cells of interest have been extracted from device 100, the collection channel 122 can be flushed to ensure that any leftover cells are cleared from the collection channel 122. This flushing can be accomplished, for example, by flowing growth media through the collection channel 122.

In some implementations, not all cells of interest are moved from the cell growth trenches 120 to the collection channel 122, and then extracted. In these implementations, some of cells in the cell growth trenches 120 are extracted. Then, the collection channel 122 is flushed, the inlet valve portion 126A and the outlet valve portion 126B of the collection channel 122 are closed, and the bridge valve portions 134 opened back up, so that additional cells of interest can be moved from the cell growth trenches 120 to the collection channel 122.

In some implementations of method 700, when any one of the inlet valve portion 116A, the outlet valve portion 116B, the inlet valve portion 126A, or the outlet valve portion 126B is opened or closed, the rest of these inlet and outlet valve portions are opened or closed. Thus, when any of the steps of method 700 refer to opening or closing any one of the inlet and outlet valve portions, that step also includes opening or closing the other inlet and outlet valve portions. However, the bridge valve portions 134 are generally controlled separately from the inlet valve portions 116A, 126A, and the outlet valve portions 116B, 126B. In other implementations, any one of the inlet valve portion 116A, the outlet valve portion 116B, the inlet valve portion 126A, or the outlet valve portion 126B can be controlled independently from the rest of the inlet valve portion 116A, the outlet valve portion 116B, the inlet valve portion 126A, or the outlet valve portion 126B. In still other implementations, the bridge valve portions 134 could be controlled together with any one of the inlet valve portion 116A, the outlet valve portion 116B, the inlet valve portion 126A, or the outlet valve portion 126B.

Thus, as shown in FIGS. 8A-8C, the various valve portions of the cell flow layer 110 allow cells to be analyzed over a long time period, and easily extracted from the device with minimal effort. The inlet valve portion 116A allows the inlet portion 114A of the growth channel 112 to be cleaned after the cells are flowed into the main portion 118 of the growth channel 112. The inlet valve portion 116A and the outlet valve portion 116B further allow growth media to be flowed into the growth channel 112 during the analysis of the cells in the cell growth trenches 120. Finally, the bridge valve portion 134 allow the collection channel 122 to remain separated from the growth channel 112 until the analysis is complete. As such, the movement path of the one or more cells of interest (the growth channel 112 and the collection channel 122) is kept substantially or wholly free of debris and contaminants (such as residual cells, bacteria, etc.). Furthermore, the bridge valve portions 134 allow the collection channel 122 and any off-chip tubing networks attached to the collection channel 122 to be cleaned in a similar manner as the inlet portion 114A of the growth channel 112. The one or more cells of interest are thus able to be easily moved from the cell growth trenches 120 to the outlet portion 124B of the collection channel 122, and extracted from the device 100 without contamination.

The arrangement of the linear cell growth trenches 120 perpendicular to the growth channel 112 enables progeny of cell lineages to be washed away by orthogonally flowing media. The continual evacuation of progeny from the cell lineages confined within the cell growth trenches 120 uniquely enables cells to be monitored for many generations (e.g., 10-100 consecutive generations for mammalian cells, and possibly over 1,000 consecutive generations for bacteria, for cells located at the termini of cell trenches), as the cells due not accumulate locally. Coupled with cleaning the inlet portion 114A and the collection channel 122, the device 100 avoids massive accumulation of cells that can occur due to exponential doubling of cells every generation. Over one billion offspring can accumulate from each initial cell after 30 generations of growth. This accumulation is avoided with device 100. The combination of features of device 100 allows for uncontaminated single-cell retrieval from cell populations imaged over many generations. In turn, a wide range of applications are enabled that were not previously possible.

The device 100 can be used in a variety of different applications. A first application is to detect small but genetically stable differences in a wide range of properties of various cells. Most cell behaviors are statistically distributed such that a given genotype gives rise to a wide range of different phenotypes. For example, the expression of proteins in cells can vary substantially even between genetically identical cells growing in the same environment. In genetic screens, rare genetic variants with desirable properties are then often outnumbered by cells that only transiently display the desirable phenotype. The device 100 enables tracking of each genetic variant for many generations of growth in multiple parallel cells and thereby provides a substantial statistical sample. The statistical sample enables genetically inherited traits to be separated from transient phenotypic variability, enabling the identification of rare variants of interest within large populations of cells that transiently mimic the interesting behavior.

Any property that can be directly or indirectly observed through microscopy can be used to record behavior, even when the genetically encoded differences between variants are small compared to the phenotypic heterogeneity in single cells. That makes it possible to detect small but genetically stable differences a wide range of properties including but not limited to gene expression, cell growth rate, morphology, cellular localization patterns, enzymatic activity, DNA replication and modification, chromosome segregation patterns, metabolic state, and cell envelopes, or any combinations thereof.

Improvements in various biological materials can be obtained by tracking properties. The biological materials can include ribonucleic acids (RNAs) and proteins, including but not limited to fluorescent or luminescent proteins; regulatory elements such as activators and repressors; optogenetically activated control proteins; enzymes and antibodies; mRNAs; small RNAs and guide RNAs for clustered regularly interspaced short palindromic repeats (CRISPR), etc.

Tracking genetic differences can include tracking changes in gene expression and reaction networks in cells, to evaluate pathways and expression programs; performing whole cell assays to measure the physiology, morphology and growth rate of cells, as well as differences between daughter cells at cell division; detecting changes in numbers or spatial distributions of organelles or other intracellular structures; and detecting cell-cell interactions and cell secretion into each trench.

Further, the device 100 allows for genetic variants of interest to be investigated without cloning the genetic variants of interest. Cloning is generally very time-consuming and resource-demanding, and may not even be possible for complex genetic mutations across one or more chromosomes, plasmids, etc. The device 100 thus makes cells of interest immediately available for further propagation, storage, downstream live-cell functional assays, and other applications.

A second application is identifying epigenetic behaviors over long time-scales (e.g., many generations). Many cellular behaviors are epigenetic, e.g., the behaviors change on a time-scale of many generations. To identify such behaviors requires an observation window of multiple generations of cell growth, in some cases tens or even hundreds of generations. The device 100 allows for the retrieval of cells after observing these long-term epigenetic changes. A variety of processes are thus enabled, including genetic screens for chromatin remodeling, cell fate decisions, bistable circuits and multigenerational oscillators, or any other epigenetic behavior that can be observed through long-term imaging.

A third application is detecting cell reactions to different environment. Many cellular behaviors depend on growth conditions. The device 100 allows multigenerational imaging under many different environments, which enables screens to first record how all observable properties of cells and cellular processes change between environments. A large number of genetic variants can be monitored in parallel, and cells for variants of interest can then be extracted.

A fourth application is performing various assays to be performed. By extracting cells physically, the device 100 allows assays beyond DNA sequencing to be performed on the extracted cells, such as genome-wide terminal assays. By extracting one of two daughter cells at each division, genome-wide time courses over cell lineages (for example tracking genome-wide properties) can be completed while simultaneously observing the properties of the daughter cells left in the device 100.

While the present disclosure has been described with reference to one or more particular implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A microfluidic device for use in analyzing cells and extracting one or more cells of interest, the microfluidic device comprising:
   a substrate;
   a cell flow layer coupled to the substrate, the cell flow layer including:
      a growth channel having a main portion and an inlet valve portion, the inlet valve portion of the growth channel being configured to aid in selectively controlling flow into the main portion of the growth channel;
      a collection channel having a main portion and an outlet valve portion, the outlet valve portion of the collection channel being configured to aid in selectively controlling flow out of the main portion of the collection channel;
      one or more bridge channels coupling the main portion of the growth channel with the main portion of the collection channel, each of the one or more bridge channels including a bridge valve portion configured to aid in selectively controlling flow between the growth channel and the collection channel; and
   a control layer coupled to the cell flow layer and configured to aid in actuating (i) the bridge valve portion of each of the one or more bridge channels, (ii) the inlet valve portion of the growth channel, and (iii) the outlet valve portion of the collection channel.

2. The microfluidic device of claim 1, further comprising one or more cell growth trenches fluidly coupled to the main portion of the growth channel, each of the one or more cell growth trenches is positioned adjacent to a first side of the main portion of the growth channel, and wherein the main portion of the collection channel is positioned adjacent to a second side of the main portion of the cell growth channel that is opposite the first side of the main portion of the growth channel, each of the one or more cell growth trenches being configured to contain there one or more cells.

3. The microfluidic device of claim 1, wherein:
   when the bridge valve portion of a respective one of the one or more bridge valves is in a first orientation, the respective one of the one or more bridge channels is open, such that fluid is allowed to flow between the growth channel and the collection channel; and
   when the bridge valve portion of the respective one of the bridge channels is in a second orientation, the respective one of the one or more bridge channels is closed, such that fluid is prevented from flowing between the growth channel and the collection channel.

4. The microfluidic device of claim 1, wherein:
   when the inlet valve portion of the growth channel is in a first orientation, fluid is prevented from flowing into the main portion of the growth channel; and
   when the inlet valve portion of the growth channel is in a second orientation, fluid is allowed to flow into the main portion of the growth channel.

5. The microfluidic device of claim 1, wherein:
   when the outlet valve portion of the collection channel is in a first orientation, fluid is prevented from flowing out of the main portion of the collection channel; and when the outlet valve portion of the collection channel is in a second orientation, fluid is allowed to flow out of the main portion of the collection channel.

6. The microfluidic device of claim 1, wherein the growth channel includes an inlet portion having a first inlet opening and a second inlet opening, and wherein when the inlet valve portion of the growth channel is in a first orientation, fluid is able to flow through the inlet portion of the growth channel between the first inlet opening and the second inlet opening, and unable to flow between the inlet portion of the growth channel and the main portion of the growth channel.

7. The microfluidic device of claim 2, wherein the cell flow layer includes an upper wall and one or more side walls, the upper wall being spaced apart from the substrate, and wherein an upper wall of each of the growth channel, the one or more cell growth trenches, the collection channel, and the one or more bridge channels is formed by the upper wall of the cell flow layer.

8. The microfluidic device of claim 7, wherein the control layer further includes a (i) first control channel configured to aid in actuating the bridge valve portion of each of the one or more bridge channels, and (ii) a second control channel configured to aid in actuating the inlet valve portion of the growth channel and the outlet valve portion of the collection channel.

9. The microfluidic device of claim 8, wherein the bridge valve portion of each respective one of the one or more bridge channels is formed at least partially by at least a portion of the upper wall of the respective one of the one or more bridge channels.

10. The microfluidic device of claim 9, wherein the first control channel of the control layer overlaps at least partially with the upper wall of each of the one or more bridge channels, the upper wall of each of the one or more bridge channels being configured to collapse toward the substrate in response to the first control channel being pressurized, thereby preventing fluid from flowing through each of the one or more bridge channels.

11. The microfluidic device of claim 8, wherein the inlet valve portion of the growth channel is formed at least partially by at least a portion the upper wall of the growth channel adjacent to the main portion of the growth channel.

12. The microfluidic device of claim 11, wherein the second control channel of the control layer overlaps at least partially with the portion of the upper wall of the growth channel that forms the inlet valve portion of the growth channel, the portion of the upper wall of the growth channel forming the inlet valve portion of the growth channel being configured to collapse toward the substrate in response to the second control channel being pressurized, thereby preventing fluid from flowing into the main portion of the growth channel.

13. The microfluidic device of claim 8, wherein the outlet valve portion of the collection channel is formed at least partially by at least a portion of the upper wall of the collection channel adjacent to the main portion of the collection channel.

14. The microfluidic device of claim 13, wherein the second control channel of the control layer overlaps at least partially with the portion of the upper wall of the collection channel that forms the outlet valve portion of the collection channel, the portion of the upper wall of the collection channel forming the outlet valve portion of the collection channel being configured to collapse toward the substrate in response to the second control channel being pressurized, thereby preventing fluid from flowing out of the main portion of the collection channel.

15. The microfluidic device of claim 1, wherein the cell flow layer and the control layer are formed from polydimethylsiloxane (PDMS), and wherein the substrate is formed from glass.

16. The microfluidic device of claim 1, wherein the main portion of the growth channel and the main portion of the collection channel each have a generally square cross-section.

17. The microfluidic device of claim 1, wherein the inlet valve portion of the growth channel, at least a portion of each of the one or more bridge channels, and the outlet valve portion of the collection channel each have a generally dome-shaped cross-section.

18. The microfluidic device of claim 1, wherein the growth channel has an outlet valve portion that selectively allows flow out of the main portion of the growth channel without flowing through the one or more bridge channels, and wherein the collection channel includes an inlet valve portion that selectively allows flow into the main portion of the collection channel without flowing through the one or more bridge channels.

19. The microfluidic device of claim 1, further comprising one or more cell growth trenches fluidly coupled to the main portion of the growth channel, each of the one or more cell growth trenches has a length of about 25.0 µm and a width of about 1.5 µm, and is spaced apart from an adjacent one of the plurality of cell growth trenches a distance of about 4.0 µm.

20. The microfluidic device of claim 1, wherein each of the one or more bridge channels has a length of about 200.0 µm, and a width of between about 50.0 µm and about 100.0 µm.

* * * * *